United States Patent
Menzaghi et al.

(10) Patent No.: US 8,217,000 B2
(45) Date of Patent: Jul. 10, 2012

(54) METHOD FOR ELEVATING PROLACTIN IN MAMMALS

(75) Inventors: Frederique Menzaghi, Rye, NY (US); Michael E. Lewis, West Chester, PA (US); Derek T. Chalmers, Riverside, CT (US)

(73) Assignee: Cara Therapeutics, Inc., Shelton, CT (US)

( * ) Notice: Subject to any disclaimer, the term of this patent is extended or adjusted under 35 U.S.C. 154(b) by 540 days.

(21) Appl. No.: 12/300,595

(22) PCT Filed: May 22, 2007

(86) PCT No.: PCT/US2007/012285
§ 371 (c)(1),
(2), (4) Date: Apr. 22, 2009

(87) PCT Pub. No.: WO2007/139826
PCT Pub. Date: Dec. 6, 2007

(65) Prior Publication Data
US 2009/0312271 A1    Dec. 17, 2009

Related U.S. Application Data

(60) Provisional application No. 60/808,677, filed on May 26, 2006.

(51) Int. Cl.
*A61K 38/02* (2006.01)
*A61K 38/07* (2006.01)

(52) U.S. Cl. .......... 514/4.7; 514/11.5; 514/21.9
(58) Field of Classification Search .......... None
See application file for complete search history.

(56) References Cited

U.S. PATENT DOCUMENTS

| 4,481,191 | A * | 11/1984 | Wei et al. | 514/15.7 |
| 5,189,064 | A * | 2/1993 | Blum et al. | 514/561 |
| 7,842,662 | B2 * | 11/2010 | Schteingart et al. | 514/6.3 |
| 2008/0132445 | A1 * | 6/2008 | Ormandy et al. | 514/12 |

OTHER PUBLICATIONS

Butelman et al. Peripheral Selectivity and Apparent Efficacy of Dynorphins . . . Drug and Alcohol Dependence. 2002, vol. 66, p. S24, Abstract No. 85.*
Krulich et al. Opioid Kappa Receptors and the Secretion of Prolactin . . . Neuroendocrinology. 1986, vol. 42, pp. 75-81.*

* cited by examiner

*Primary Examiner* — Jeffrey E Russel
(74) *Attorney, Agent, or Firm* — Algis Anilionis; F. Chau & Associates, LLC

(57) ABSTRACT

Methods for elevating and stabilizing prolactin levels in a mammal including methods of treating disorders and conditions associated with reduced serum levels of prolactin are provided. Also provided are methods of using certain synthetic tetrapeptide amides which are peripherally selective kappa opioid receptor agonists to elevate or stabilize serum prolactin levels.

22 Claims, 7 Drawing Sheets

Arithmetic Mean Changes from Baseline (Pre dose) in Serum Prolactin Concentrations Following a 1 hour IV Infusion in Female Subjects (Part A)

● Placebo (1-hour infusion)    ○ 0.24 mg/kg CR665 (1-hour infusion)

Figure 1: Arithmetic Mean Changes from Baseline (Pre dose) in Serum Prolactin Concentrations Following a 1 hour IV Infusion in Male Subjects (Part A)

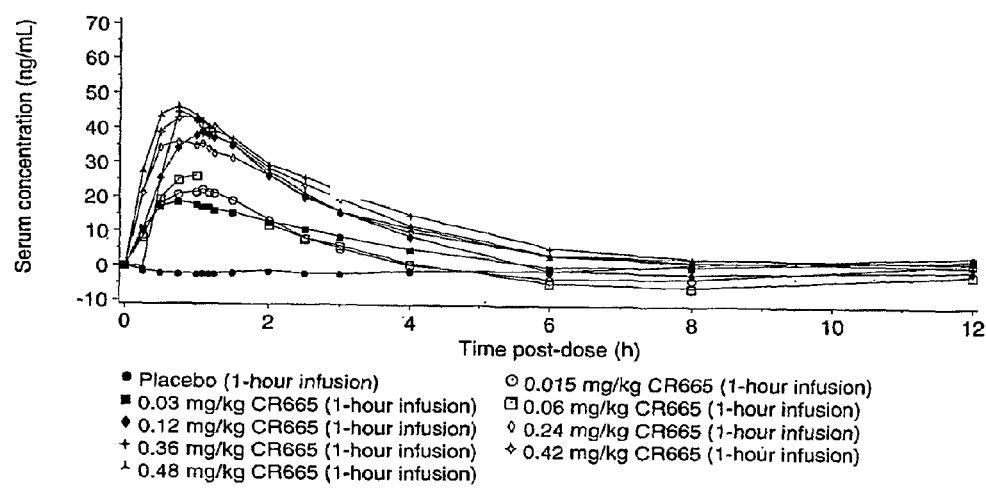

- Placebo (1-hour infusion)
- 0.03 mg/kg CR665 (1-hour infusion)
- 0.12 mg/kg CR665 (1-hour infusion)
- 0.36 mg/kg CR665 (1-hour infusion)
- 0.48 mg/kg CR665 (1-hour infusion)
- 0.015 mg/kg CR665 (1-hour infusion)
- 0.06 mg/kg CR665 (1-hour infusion)
- 0.24 mg/kg CR665 (1-hour infusion)
- 0.42 mg/kg CR665 (1-hour infusion)

Figure 2: Arithmetic Mean Changes from Baseline (Pre dose) in Serum Prolactin Concentrations Following a 1 hour IV Infusion in Female Subjects (Part A)

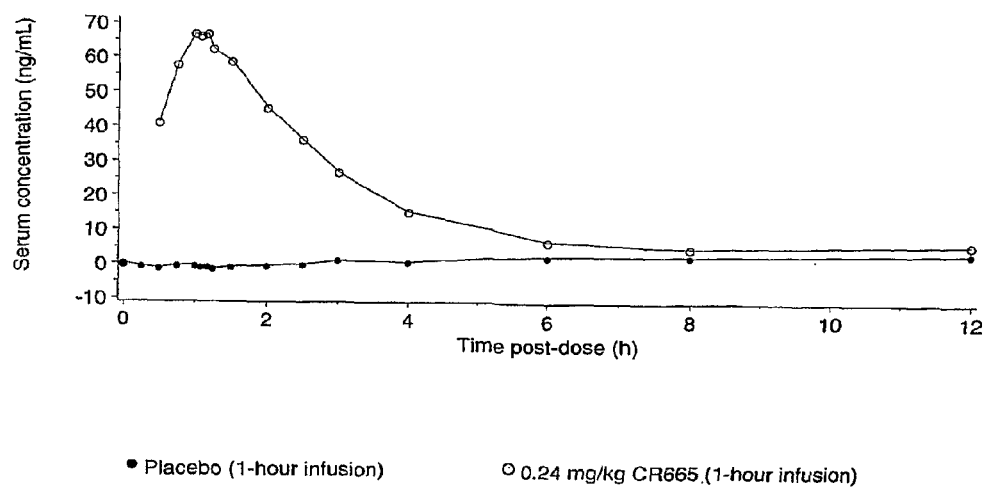

- Placebo (1-hour infusion)
- 0.24 mg/kg CR665 (1-hour infusion)

Figure 3: Arithmetic Mean Changes from Baseline (Pre dose) in Serum Prolactin Concentrations Following a 5 minute IV Infusion in Male Subjects (Part B)

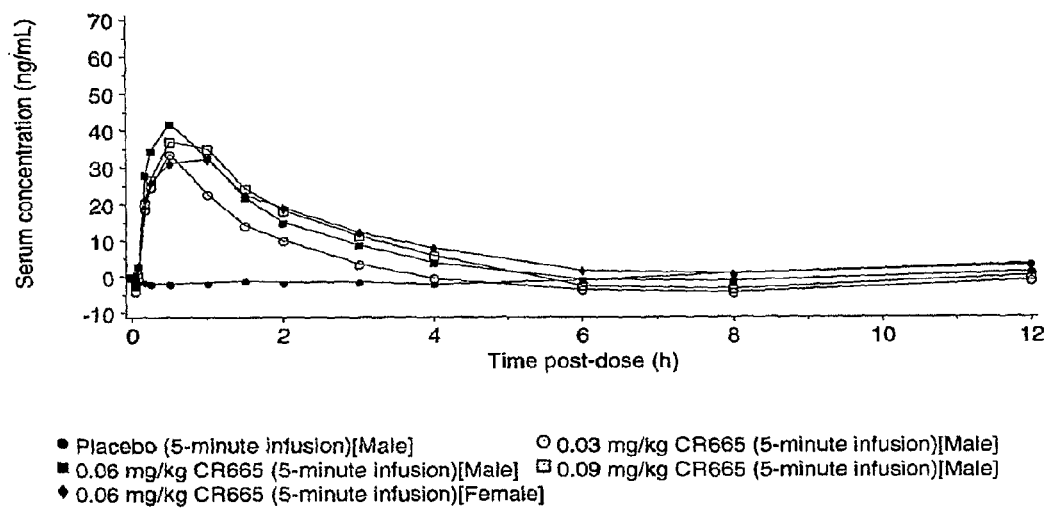

● Placebo (5-minute infusion)[Male]   ○ 0.03 mg/kg CR665 (5-minute infusion)[Male]
■ 0.06 mg/kg CR665 (5-minute infusion)[Male]   □ 0.09 mg/kg CR665 (5-minute infusion)[Male]
♦ 0.06 mg/kg CR665 (5-minute infusion)[Female]

Figure 4: Geometric Mean Plasma Concentrations of CR665 Following a 1 hour IV Infusion in Male Subjects (Part A) (Linear Scale)

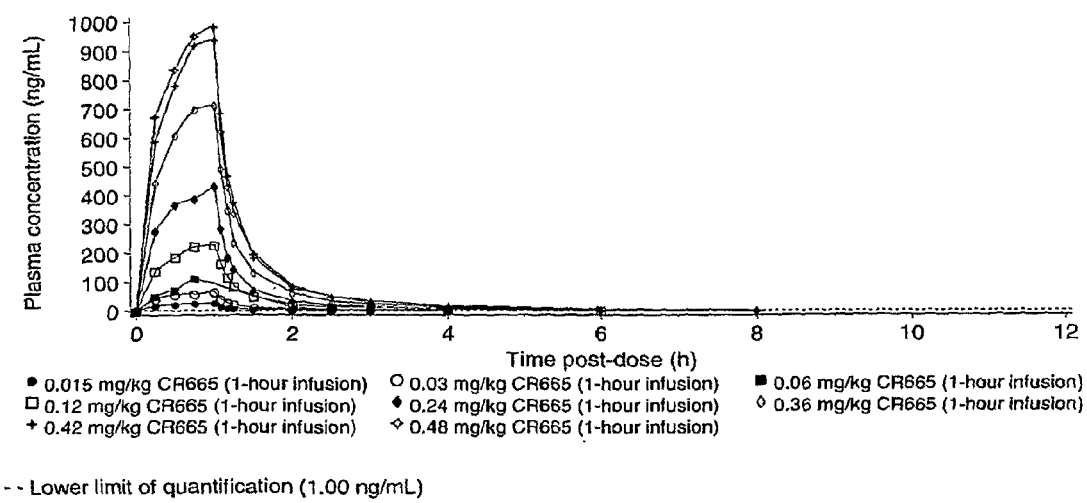

● 0.015 mg/kg CR665 (1-hour infusion)   ○ 0.03 mg/kg CR665 (1-hour infusion)   ■ 0.06 mg/kg CR665 (1-hour infusion)
□ 0.12 mg/kg CR665 (1-hour infusion)   ♦ 0.24 mg/kg CR665 (1-hour infusion)   ◊ 0.36 mg/kg CR665 (1-hour infusion)
+ 0.42 mg/kg CR665 (1-hour infusion)   ◇ 0.48 mg/kg CR665 (1-hour infusion)

- - - Lower limit of quantification (1.00 ng/mL)

Figure 5: Geometric Mean Plasma Concentrations of CR665 Following a 1 hour IV Infusion in Male Subjects (Part A) (Semi logarithmic Scale)

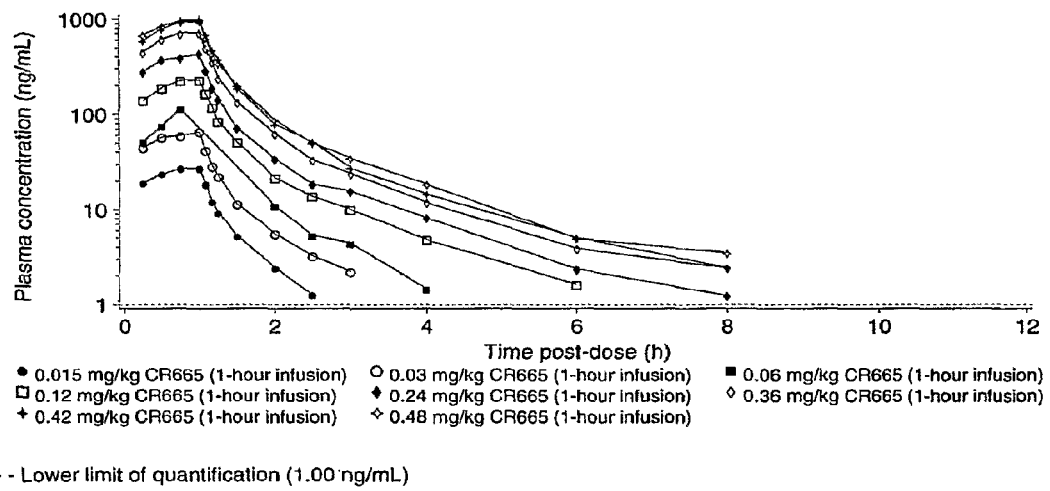

- • 0.015 mg/kg CR665 (1-hour infusion)
- ○ 0.03 mg/kg CR665 (1-hour infusion)
- ■ 0.06 mg/kg CR665 (1-hour infusion)
- □ 0.12 mg/kg CR665 (1-hour infusion)
- ♦ 0.24 mg/kg CR665 (1-hour infusion)
- ◊ 0.36 mg/kg CR665 (1-hour infusion)
- + 0.42 mg/kg CR665 (1-hour infusion)
- ⋄ 0.48 mg/kg CR665 (1-hour infusion)

--- Lower limit of quantification (1.00 ng/mL)

Figure 6: Geometric Mean $AUC_{0-\infty}$ for CR665 Versus Dose Level Following a 1 hour IV Infusion in Male Subjects (Part A)

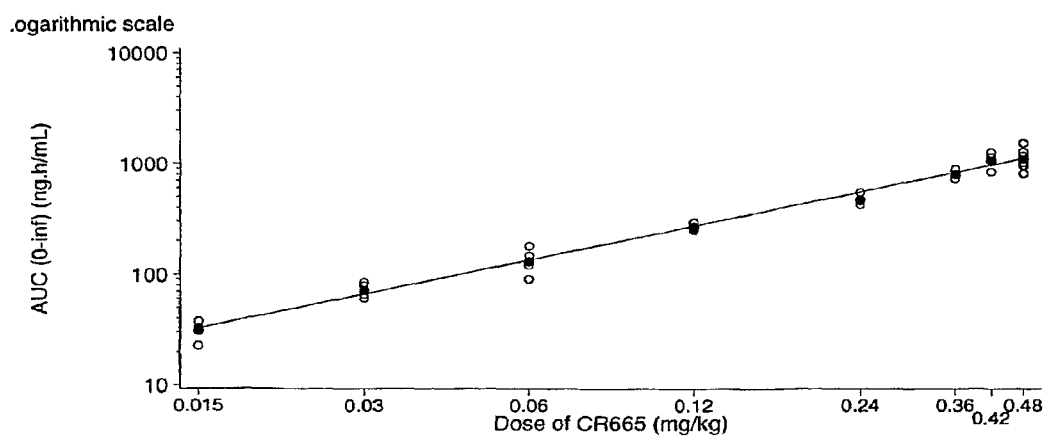

Figure 7: Geometric Mean Plasma Concentrations of CR665 Following a 1 hour IV Infusion of 0.24 mg/kg CR665 in Female Subjects (Part A) (Linear Scale)

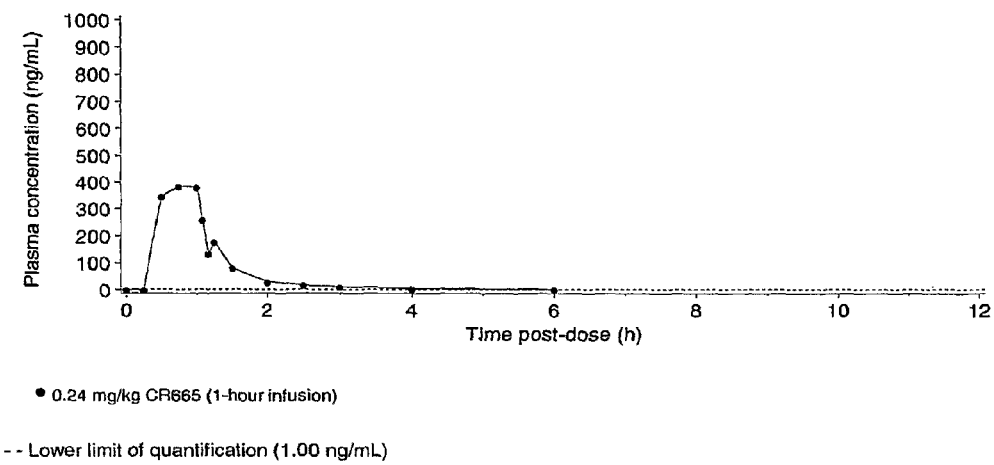

• 0.24 mg/kg CR665 (1-hour infusion)

- - - Lower limit of quantification (1.00 ng/mL)

Figure 8: Geometric Mean Plasma Concentrations of CR665 Following a 1 hour IV Infusion of 0.24 mg/kg CR665 in Female Subjects (Part A) (Semi logarithmic Scale)

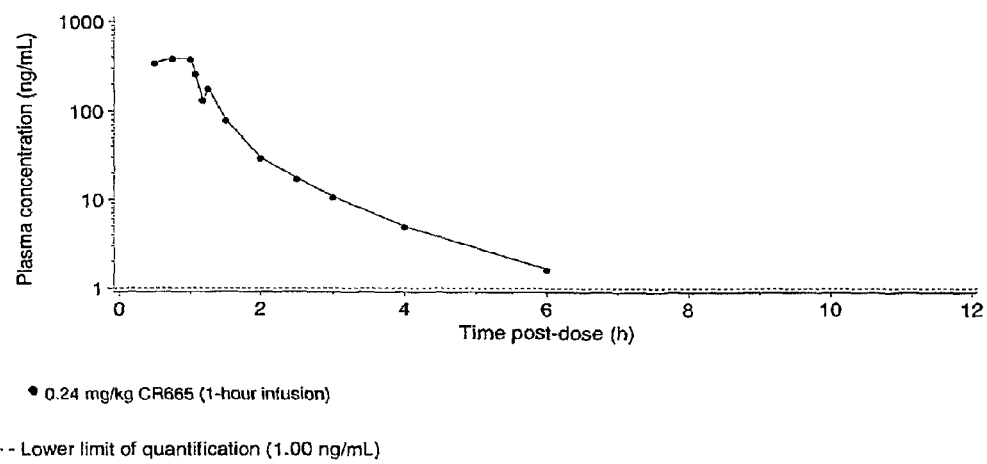

• 0.24 mg/kg CR665 (1-hour infusion)

- - - Lower limit of quantification (1.00 ng/mL)

Figure 9: Arithmetic Mean (±SD) Plasma Concentrations of CR665 Following a 1-hour IV Infusion of 0.24 mg/kg CR665 in Male and Female Subjects (Part A) (Linear Scale)
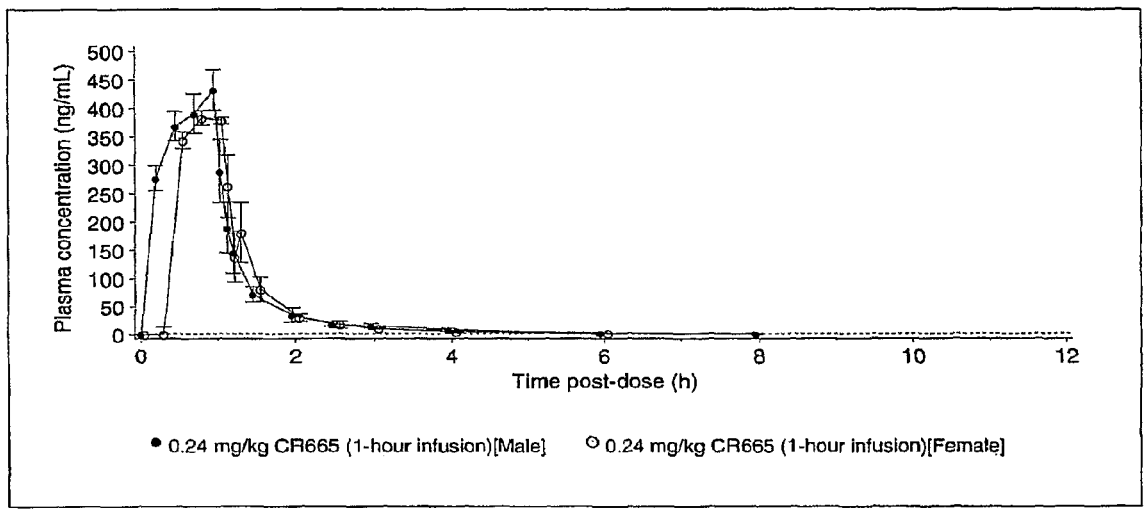
Figure 10: Geometric Mean Plasma Concentrations of CR665 Following a 5-minute IV Infusion in Male and Female Subjects (Part B) (Linear Scale)
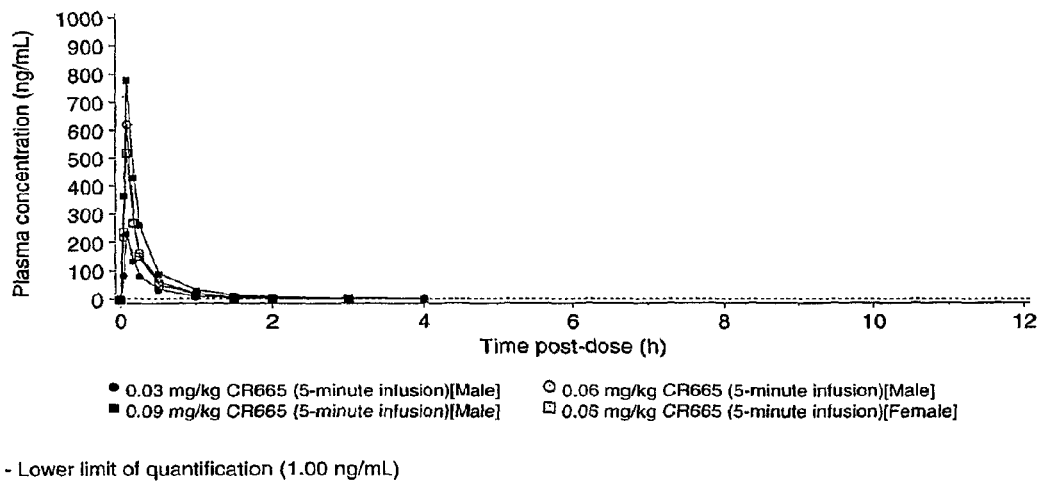

Figure 11: Geometric Mean Plasma Concentrations of CR665 Following a 5-minute IV Infusion in Male and Female Subjects (Part B) (Semi logarithmic Scale)
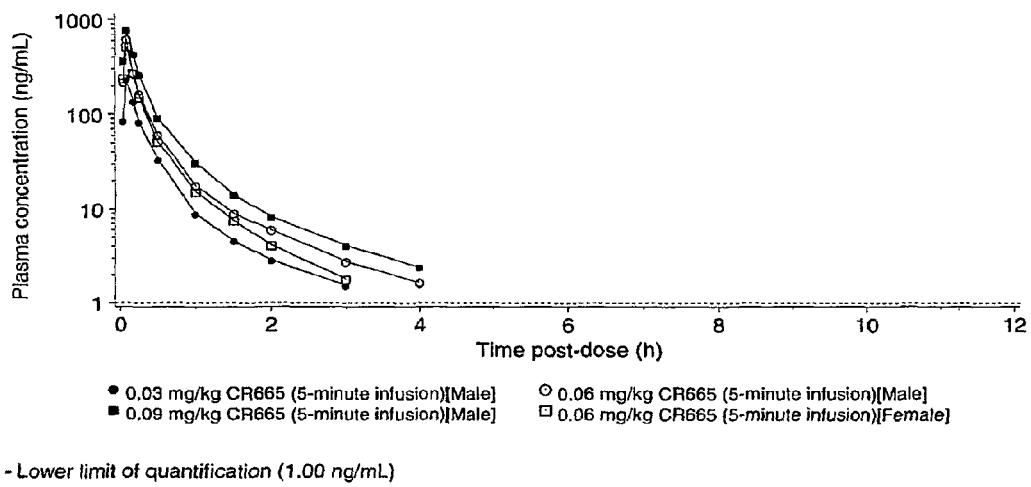
Figure 12: Geometric Mean $AUC_{0-\infty}$ for CR665 Versus Dose Level Following a 5-minute IV Infusion in Male Subjects (Part B)
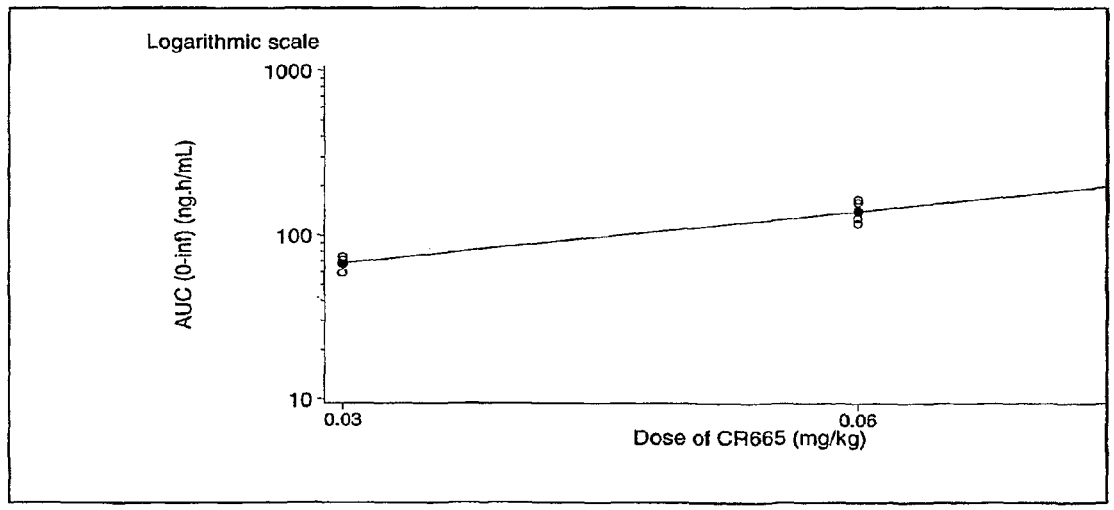

Figure 13: Relationship Between $AUC_{0-12h}$ of Changes from Baseline in Serum Prolactin and $AUC_{0-\infty}$ of CR665 over the 0.015 to 0.36 mg/kg Dose Range in Male Subjects (Part A)

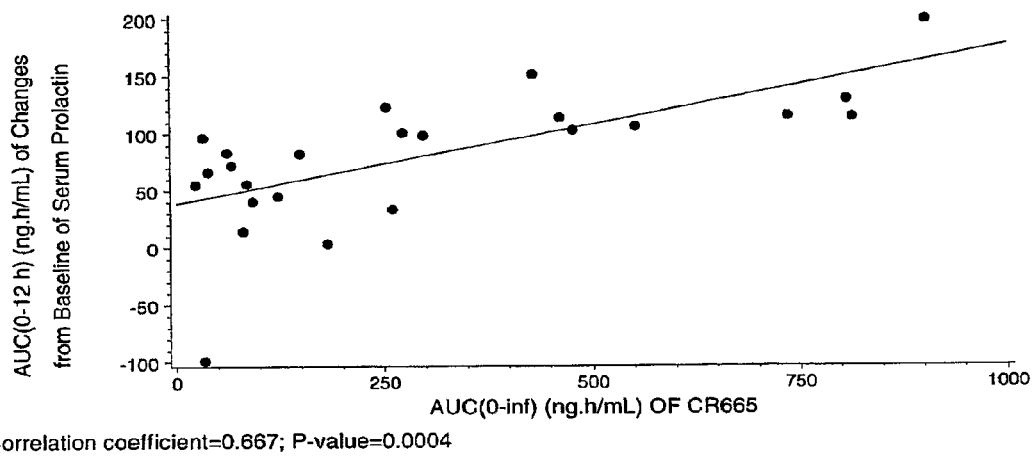

Correlation coefficient=0.667; P-value=0.0004

Figure 14: Relationship Between Cmax of Changes from Baseline in Serum Prolactin and Cmax of CR665 over the 0.015 to 0.36 mg/kg Dose Range in Male Subjects (Part A)

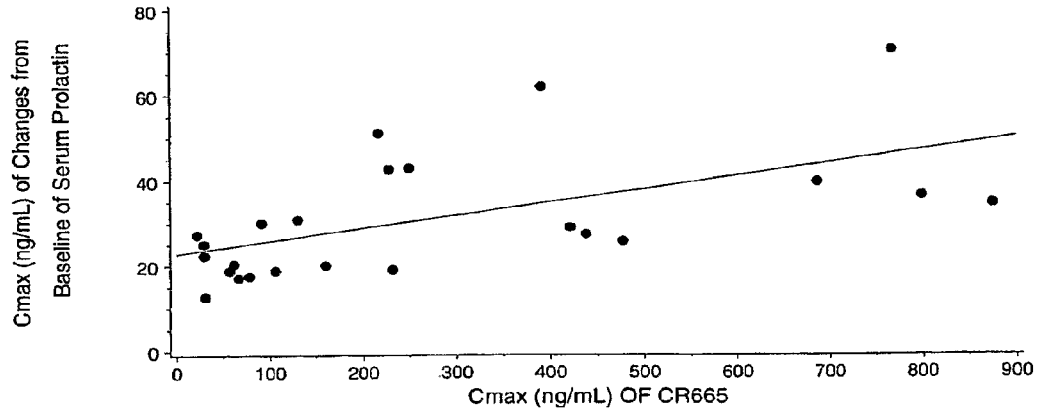

Correlation coefficient=0.565; P-value=0.0040

METHOD FOR ELEVATING PROLACTIN IN MAMMALS

CROSS-REFERENCE TO RELATED APPLICATIONS

This Application claims priority to and incorporates by reference herein U.S. Provisional Application Ser. No. 60/808,677 filed May 26, 2006 and entitled "METHOD FOR ELEVATING PROLACTIN IN MAMMALS."

BACKGROUND OF THE INVENTION

1. Field of the Invention

The invention relates to the use of peripherally selective kappa opioid receptor agonists to elevate serum levels of prolactin for the benefit of a mammal in need of such elevation.

2. Background

Prolactin is a 198 amino acid polypeptide synthesized in pituitary lactotrophs, which constitute about 20 percent of adenohypophysial cells (for review, see *Harrison's Principles of Internal Medicine,* 16th Ed., p. 2084; also Freeman M E et al. Prolactin: Structure, function, and regulation of secretion. *Physiol. Rev.* 80: 1523 1631, 2000). Prolactin is also referred to in the art as Galactin, Lactogen, Lactoropin, LMTH, LTH, Luteomammotrophic Hormone, Luteotrophic Hormone, Luteotropin, and Mammotrophin, although these names are now obsolete. The best studied effects of prolactin are on the mammary gland, and include growth and development of the mammary gland (mammogenesis), synthesis of milk (lactogenesis), and maintenance of milk secretion (galactopoiesis). The endocrine control of lactation involves multiple complex physiological mechanisms since mammogenesis, lactogenesis, galactopoiesis, and galactokinesis are all essential for proper lactation. Prolactin is the key hormone of lactation and is believed to be the single most important galactopoietic hormone. Oxytocin, serotonin, opioid peptides, histamine, substance P, and other physiological substances modulate prolactin release by means of an autocrine/paracrine mechanism at the level of the hypothalamus, whereas estrogen and progesterone hormones can act at the hypothalamic and adenohypophysial levels. Human placental lactogen and growth factors play an essential role in successful lactation during pregnancy, with oxytocin functioning as a key galactokinetic hormone.

Normal adult serum prolactin levels are about 10-25 ng/ml in women and 10-20 ng/ml in men. Prolactin is secreted in an episodic manner with a distinct 24 hour pattern. Circulating prolactin levels are lowest at midday, and a modest increase occurs during the afternoon. Prolactin levels increase shortly after onset of sleep, peaking in the early morning. Serum prolactin levels rise substantially during pregnancy (150-200 ng/ml) and decline rapidly within two weeks of parturition. Breastfeeding will normally cause prolactin levels to remain elevated, due to suckling induced activation of neural reflexes that that induce prolactin release. However, inadequate activation of prolactin release will interfere with breastfeeding, with a variety of potentially deleterious psychological and physiological consequences, e.g., a failure of mother infant bonding and a failure to transmit maternal protective antibodies to the infant (American Academy of Pediatrics, Section on Breastfeeding. Breastfeeding and the use of human milk. Pediatrics 115: 496-506, 2005). According to the American Academy of Pediatrics, in this most current version of their guidance on breastfeeding, "Extensive research using improved epidemiologic methods and modern laboratory techniques documents diverse and compelling advantages for infants, mothers, families, and society from breastfeeding and use of human milk for infant feeding. These advantages include health, nutritional, immunologic, developmental, psychologic, social, economic, and environmental benefits." Because of the well documented benefits of breastfeeding, insufficient lactation is now viewed as an important medical problem.

There are numerous risk factors for insufficient lactation, including:

(i) restarting lactation after termination, e.g., to care for a sick infant (Thompson N Relactation in a newborn intensive care setting. *J. Hum. Lact.* 12: 233-235, 1996).

(ii) physical abnormality of the breast (Neifert M R et al. Lactation failure due to insufficient glandular development of the breast. *Pediatrics* 76:823-828, 1985).

(iii) absence of breast enlargement during pregnancy (Moon J et al. Breast engorgement: contributing variables and variables amenable to nursing intervention. *J. Obstet. Gynecol. Neonatal Nurs.* 18: 309-315, 1989).

(iv) history of breast surgery (Widdice L The effects of breast reduction and breast augmentation surgery on lactation: An annotated bibliography. *J. Hum. Lact.* 9:161-163, 1993).

(v) first time delivery of infant (Dewey K G et al. Risk factors for suboptimal infant breastfeeding behavior, delayed onset of lactation, and excess neonatal weight loss. *Pediatrics* 112:607-619, 2003).

(vi) premature delivery of infant (Ehrenkranz R A et al. Metoclopramide effect on faltering milk production by mothers of premature infants. *Pediatrics;* 78:614-20, 1986; Feher S D K et al. Increasing breast milk production for premature infants with a relaxation/imagery audiotape. *Pediatrics* 83:57-60, 1989).

(vii) delivery of more than one infant (Leonard, L. Breastfeeding higher order multiples: Enhancing support during the postpartum hospitalization period. *J. Hum. Lact.* 18:386-392, 2002).

(viii) adoption of infant (Cheales Siebenaler, N. Induced lactation in an adoptive mother. *J. Hum. Lact.* 15:41-43, 1999).

(ix) retention of placental fragments (Neifert, M R et al. Failure of lactogenesis associated with placental retention. *Am. J. Obstet. Gynecol.* 140:477-478, 1981).

(x) use of hormonal birth control (Tankeyoon M et al. Effects of hormonal contraceptives on milk volume and infant growth. WHO Special Programme of Research, Development and Research Training in Human Reproduction Task force on oral contraceptives. *Contraception* 30:505-22, 1984).

(xi) use of certain OTC decongestants (Aljazaf K et al. Pseudoephedrine: effects on milk production in women and estimation of infant exposure via breastmilk. *Br. J. Clin. Pharmacol.* 56:18-24, 2003).

(xii) cigarette smoking (Andersen A N et al: Suppressed prolactin but normal neurophysin levels in cigarette smoking breast feeding women. *Clin. Endocrinol. (Oxf.)* 17:363-8, 1982).

(xiii) prepregnant overweight and obesity (Hilson J A et al. High prepregnant body mass index is associated with poor lactation outcomes among white, rural women independent of psychosocial and demographic correlates. *J. Hum. Lact.* 20:18-29, 2004; Rasmussen K M et al. Prepregnant overweight and obesity diminish the prolactin response to suckling in the first week postpartum. *Pediatrics* 113:465-71, 2004).

(xiv) Cesarean delivery (Chapman D J et al. Identification of risk factors for delayed onset of lactation. *J. Am. Diet. Assoc.* 99:450-454, 1999).

(xv) insulin dependent maternal diabetes (Neubauer, S H et al. Delayed lactogenesis in women with insulin dependent diabetes mellitus. *Am. J. Clin. Nutr.* 58:54-60, 1993).

(xvi) medications to treat labor pain (Riordan J et al. The effect of labor pain relief medication on neonatal suckling and breastfeeding duration. *J. Hum. Lact.* 16:7-12, 2000; Ransjo Arvidson A B et al. Maternal analgesia during labor disturbs newborn behavior: effects on breastfeeding, temperature, and crying. *Birth* 28:5-12; 2001).

(xvii) stress (Chen D C et al. Stress during labor and delivery and early lactation performance. *Am. J. Clin. Nutr.* 68:335-344, 1998; Dewey K. Maternal and fetal stress are associated with impaired lactogenesis in humans. *J. Nutr.* 131:3012 S-3015S, 2001).

Signs of insufficient lactation in a human infant include: (1) insufficient weight gain in an infant who is receiving food only by breast feeding, even if the infant appears content; (2) infant latching on poorly; (3) infant sucking inconsistently; (4) inconsistency of let down reflex, and (5) evidence of hunger, indicated by crying soon after feedings.

Lactation failure in humans is a common clinical event with serious emotional sequelae. It has been considered to be a significant problem in 5 to 10% of all lactations. In many instances this leads to premature initiation of supplements or total weaning. This is considered to be an inferior child rearing practice and may be harmful to certain infants with an increased risk of gastritis and other disorders. Many affected women are severely emotionally distressed by their perceived inadequacy, thus affecting the parent child bond. Failure to thrive in infants is not uncommon if the mother refuses to supplement.

There has therefore been a long need for a medicament that can promote human lactation, e.g., when there is insufficient lactation after the birth of the child. For animal breeders, the inability of their livestock, e.g., mares, to produce and secrete milk after giving birth can be a significant problem. Should the breeding animals not lactate properly, the offspring must then be bottle fed, which is time consuming, labor intensive, and costly; thus, there is a need for a medicament to safely and effectively promote breeding animal lactation. For commercial milk producing animals like cows and goats, there is an economic need to safely and effectively increase their milk production above a normal level.

A number of causes of reductions in prolactin levels that are associated with insufficient lactation were noted above. Certain of these causes are also associated with reduced prolactin levels in non-lactating subjects, e.g., cigarette smoking (Fuxe K et al. Neuroendocrine actions of nicotine and of exposure to cigarette smoke: medical implications. *Psychoneuroendocrinology* 14: 1.9-41, 1989). Other causes of low prolactin levels (hypoprolactinemia) include the use of various therapeutic agents, such as L deprenyl for the treatment of migraine (Fanciullacci M et al. Dopamine involvement in the migraine attack. *Funct Neurol.* 15 Suppl 3:171-81, 2000). Hypoprolactinemia of unknown origin has also been associated with poor sperm motility in adult men (Gonzales G F et al. Hypoprolactinemia as related to seminal quality and serum testosterone. *Arch. Androl.* 23:259-65, 1989), a finding that is supported by the observation that pharmacological suppression of prolactin release for several weeks in young men decreased subsequent hCG stimulated testosterone secretion (Oseko F et al. Effects of chronic bromocriptine induced hypoprolactinemia on plasma testosterone responses to human chorionic gonadotropin stimulation in normal men. *Fertil. Steril.* 55:355-357, 1991). Hypoprolactinemia could also contribute to age related changes in physiological functions. Serum prolactin concentrations tend to fall with age, e.g. in older men and estrogen unreplaced postmenopausal women (Maddox P et al. Bioactive and immunoactive prolactin levels after TRH stimulation in the sera of normal women. *Horm. Metab. Res.* 24:181-184, 1992; Maddox P et al. Basal prolactin and total lactogenic hormone levels by microbioassay and immunoassay in normal human sera. *Acta Endocrinol. (Copenh.)* 125:621-627, 1991). Remarkably, a comparable quantitative reduction in prolactin secretion occurs in critically ill individuals (Van den Berghe G et al. Thyrotropin and prolactin release in prolonged critical illness—dynamics of spontaneous secretion and effects of growth hormone secretagogues. *Clin. Endocrinol. (Oxf.)* 47:599-612, 1998) as well as in patients with poorly controlled type I diabetes mellitus (Iranmanesh A et al. Attenuated pulsatile release of prolactin in men with insulin dependent diabetes mellitus. *J. Clin. Endocrinol Metab.* 71:73-78, 1990). Hypoprolactinemia is also reported to be a risk factor for prolonged lymphopenia and apoptosis associated depletion of lymphoid organs in nosocomial sepsis related death in critically ill children (Felmet K A et al. Prolonged lymphopenia, lymphoid depletion, and hypoprolactinemia in children with nosocomial sepsis and multiple organ failure. *J. Immunol.* 174:3765-72, 2005). The findings reviewed above indicate that prolactin deficiency may contribute to impaired testosterone dependent functioning and age related changes as well as vulnerability to illness.

In addition to the apparent roles of prolactin discussed above, there is evidence that prolactin is important for maintenance of rapid eye movement sleep (REM sleep), which is essential for normal brain function. After observing that pregnancy associated sleep enhancement is correlated with the daily surges of prolactin, investigators found that administration of prolactin to female rats significantly increased REM sleep (Zhang S Q et al. Effects of prolactin on sleep in cyclic rats. *Psychiatry Clin. Neurosci.* 53:101-3, 1999). Consistent with these findings, induction of experimental hypoprolactinemia in male rats was found to decrease REM sleep (Obál Jr F et al. Antiserum to prolactin decreases rapid eye movement sleep (REM sleep) in the male rat. *Physiol. Behav.* 52:1063-1068, 1992). These findings indicate that subjects experiencing insufficient REM sleep could benefit from elevations in prolactin.

Based on the findings reviewed above, there is a need for a medicament that can safely and effectively elevate prolactin level in a variety of subjects with functional hypoprolactinemia, particularly including females experiencing insufficient lactation, but also males experiencing insufficient testosterone related functions, and both females and males who are suffering from the effects of severe illness, including type I diabetes, or who are suffering the effects of insufficient REM sleep, e.g., due to insomnia.

The citation of any reference herein should not be construed as an admission that such reference is available as "Prior Art" to the instant application.

SUMMARY OF THE INVENTION

In general, the invention provides methods for treating a subject suffering from insufficient or inadequate serum prolactin, such as functional hypoprolactinemia and the disorders disclosed herein and known in the art associated with insufficient or inadequate serum prolactin, as well as methods for treating a subject in need of elevated or stabilized levels of prolactin. In one embodiment, a method employs a peripherally selective kappa opioid receptor agonist compound, optionally in a pharmaceutically acceptable vehicle for local, regional or systemic administration, said compound possessing prolactin elevating, increasing or stabilizing activity, optionally administered without causing a severe or a clinically significant side effect, such as CNS effects or diuretic effects.

In another embodiment, the invention features a method of treating functional hypoprolactinemia in a subject with a formulation of a peripherally selective kappa opioid receptor agonist, optionally suitable for incorporation into a controlled drug delivery device. In a particular aspect, a controlled drug delivery device is applied to the skin of a subject. In certain embodiments, a controlled drug delivery device is applied to the skin of a subject and optionally further utilizes iontophoresis to increase transdermal drug delivery.

In certain embodiments, a formulation is a solid or liquid or gel.

In certain embodiments, a formulation includes a liquid carrier.

In certain embodiments, a therapeutically effective dose of a peripherally selective kappa opioid receptor agonist is selected to produce elevated, increased or stabilized serum prolactin levels without producing severe or significant diuresis and/or a CNS side effect.

In certain embodiments, a peripherally selective kappa opioid receptor agonist produces pharmacologically insignificant or physiologically tolerable levels of said agonist in the plasma of an infant consuming the breast milk from or produced by a subject treated with said agonist.

In certain embodiments, the peripherally selective kappa opioid receptor agonist is selected to avoid producing a severe or a clinically significant side effect in an infant consuming the breast milk from or produced by a subject treated with said agonist.

In certain aspects, the invention features methods of elevating, increasing or stabilizing plasma levels of prolactin to a subject in need of elevated, increased or stabilized prolactin. In one embodiment, a method includes administration of a therapeutically effective dose of a peripherally selective kappa opioid receptor agonist to the subject. In another embodiment, a method includes administration of a therapeutically effective dose of a peripherally selective kappa opioid receptor agonist to the subject, in combination with a prolactin elevating-increasing or stabilizing dose of a second compound selected from a D2 dopamine receptor antagonist, mu opioid receptor agonist, or prolactin.

In various embodiments a subject is: a person, e.g., a human patient, in need of elevated prolactin levels. E.g., the subject can be: a person in need of stimulation of lactation or stabilization of lactation, e.g., a mother.

The invention features methods for treatment and/or prevention of lactational failure, which can be diagnosed by various criteria, including:
 a) baby is dissatisfied and irritable after breast feeding;
 b) poor infant weight gain in relation to age/length;
 c) lack of breast engorgement/leaking if feeding is missed;
 d) baby is satisfied by supplemental feeding following breast feeding;
 e) milk secretion of less than 500 ml/day.

These methods involve systemic administration of compositions that contain one or more compounds that exert prolactin elevating, increasing or stabilizing activity via kappa opiate receptors, but that do not exhibit a severe or significant side effect, such as a CNS or diuretic effect at effective dosages.

In various embodiments, methods use compositions containing peripherally selective kappa opioid receptor agonists that do not, upon systemic administration, evoke severe or clinically significant diuresis or CNS effects, as defined herein, particularly at the prolactin elevating dosage. Compositions that contain a peripherally selective kappa opioid receptor agonist together with other prolactin elevating compounds are also provided.

Typically, compounds intended for use in the compositions and methods herein possess prolactin elevating, increasing or stabilizing activity and reduced or tolerable CNS effects, as defined herein, because, without being bound by any theory, they do not substantially cross the blood brain barrier. A relative or complete absence of substantial crossing of the blood brain barrier lessens the occurrence of CNS systemic effects. Kappa opioid receptors agonists that readily cross the blood brain barrier could be effective as prolactin elevating agents, but permeability through the blood brain barrier can result in severe or intolerable side effects, such as dysphoria and hallucinations.

Peripherally selective kappa opioid receptor agonists include kappa opioid receptor agonists that do not substantially cross the blood brain barrier as assessed by assays described herein or known in the art. The peripherally selective kappa opioid receptor agonists for use in the methods and compositions provided herein also include any compound that by virtue of its interaction, either directly or indirectly, with peripheral kappa opioid receptor receptors ameliorates failure of lactation, or elevates, increases or stabilizes levels of serum prolactin, without exhibiting medically severe or significant CNS effects, such as dysphoria and hallucinations, at effective doses.

As used herein, the term "peripherally selective," when used in reference to a "kappa opioid receptor agonist" refers to a chemical compound having a reduced ability to cross (traverse) the blood-brain barrier, or that exhibits little or substantially no crossing of the blood-brain barrier when not administered to the CNS (brain and spinal cord). As a consequence of a reduced ability or inability to cross (traverse) the blood-brain barrier, a peripherally selective kappa opioid receptor agonist typically exhibits fewer or less severe (minor or tolerable) side effects in the CNS, such as dysphoria, hallucinations, or sedation.

Various measures of the ability of a compound to cross (traverse) the blood-brain barrier are known in the art and can be used to measure the amount or rate (kinetics) of blood-brain barrier crossing (traversal). One non-limiting example is to compare the ability of a compound to elicit peripheral effects versus the ability of the compound to elicit central effects following treatment with a particular compound (e.g., kappa opioid receptor agonist). Peripheral effects can be measured using the mouse writhing test (WT) and central effects, due to action of kappa opioid receptors located in the brain and spinal cord, can be measured using the mouse tail-flick test (TF).

In brief, the mouse writhing test (WT) test (described in Bentley et al., *Br. J. Phamac.*, 73:325 (1981)) employs conscious male ICR mice (available from Harlan) weighing about 20 to 30 grams. Mice are fasted for about 12 to 16 hours prior to the test and writhing is induced by intraperitoneal administration of dilute acetic acid (10 ml of 0.6% aqueous acetic acid/kg body weight). Writhing is scored during the 15 minutes following acetic acid administration. Compounds (e.g., kappa opioid receptor agonists) are typically tested at 3 to 4 increasing doses, given by intravenous route, and at a unique pretreatment time (e.g., −5 minutes before acetic acid injection). This step is used to determine the potency (WT-$ED_{50}$) as well as a submaximal effective dose (about 80-90% antinociception). In a second step, a submaximal effective dose for each specific compound is administered at various pretreatment times (e.g., −5 minutes, −60 minutes, −120 minutes and −180 minutes) prior to the administration of the acetic acid in order to determine the duration of action. Throughout the test, a control group of mice are used which are administered only the vehicle without the compound. The number of writhes are counted over a 15-minute period, starting from the time of acetic acid injection, and bioactivity, i.e. antinociception, is expressed as a percentage, and is calculated as follows:

100×(writhes in control group-writhes in treated group)/writhes in control group.

Because each submaximal dose likely varies so as not to be directly comparable, results are normalized mathematically, to provide comparable values. Values higher than 100% indicate greater antinociception than at the beginning of the study. Compounds effective at reducing writhing by at least about 25% at a time of 1 hour are considered to have long duration of in vivo action.

In addition to using the writhing test to determine duration of antinociceptive activity, it is also used to measure the in vivo biopotency (short term) of the peptide. This value is represented as WT-$ED_{50}$ in milligrams per kg of body weight, a measure of the dosage necessary to reduce the number of writhes in the mouse being tested by 50% (as compared to a control mouse) over a period of 15 minutes.

The tail-flick test (TF) is an assay of acute somatic pain, designed to evaluate potency and duration of action of centrally acting analgesics (described, for example, in Vanderah, et al., *J. Pharm. Exper. Therapeutics,* 262:190 (1992)). Nociception induced by tail-dip into hot water (52° C.) results in a rapid tail withdrawal, or a "tail-flick." Centrally acting compounds are expected to increase, in a dose-related manner, the latency for tail withdrawal.

"Brain Penetration Index" (BPI) can be used to provide a numerical representation of whether a compound functions centrally or peripherally. BPI is defined as: BPI=TF-$ED_{50}$/WT-$ED_{50}$; where the $ED_{50}$ values are the doses that produce half maximal effect in the mouse writhing test (WT-$ED_{50}$) and the mouse tail-flick test (TF-$ED_{50}$), respectively, when administered intravenously. A high BPI value reflects low brain penetration and, therefore, a compound that is less likely to substantially cross the blood-brain barrier or produce severe CNS side effects. BPI values lower than 5 indicate significant or substantial brain penetration, and, therefore, a compound that is likely to substantially cross the blood-brain barrier, which can result in severe side effects (e.g., dysphoria, hallucinations and sedation) when used clinically. Accordingly, compounds useful in the invention have BPI values typically greater than 5, or more, for example, BPI values of, 10, 15, 20, 25, 30, 40, 45, 50, 60, 75, 100, 125, 150, 175, 200, 225, 250, 275, 300, 400, 500, 600, 700, 800, 900, 1000, 1500, 2000, or more.

Particular non-limiting compounds of the invention are disclosed in U.S. Pat. No. 5,965,701, are sequences of four D-isomer amino acid residues having a C-terminus which is a mono or di-substituted amide. Representative compounds, which have an affinity for the kappa opioid receptor at least 1,000 times their affinity for the mu opioid receptor and an $ED_{50}$ of not greater than about 0.5 mg/kg, include H-D-Phe-D-Phe-D-Nle-D-Arg-NHEt, H-D-Phe-D-Phe-D-Nle-D-Arg-morpholinyl, H-D-Phe-D-Phe-D-Nle-D-Arg-NH-4-picolyl, H-D-Phe-D-Phe-D-Nle-D-Arg-NHPr, H-D-Phe-D-Phe-D-Nle-D-Arg-thiomorpholinyl, H-D-Phe-D-Phe-D-Nle-D-Arg-NEt$_2$, H-D-Phe-D-Phe-D-Nle-D-Arg-NHMe, H-D-Phe-D-Phe-D-Leu-D-Orn-morpholinyl, H-D-Phe-D-Phe-D-Nle-D-Arg-NHhEt, H-D-Phe-D-Phe-D-Nle-D-Arg-NH-cyclopropyl, H-D-Ala(2Thi)-D-4 Cpa-D-Leu-D-Arg-morpholinyl, H-D-Phe-D-Phe-D-Nle-D-Arg-piperidinyl, H-D-Phe-D-Phe-D-Leu-D-Orn-NHEt, H-D-Phe-D-Phe-D-Leu-D-Lys-morpholinyl, and H-D-Phe-D-Phe-D-Nle-D-Arg-piperazinyl.

Peripherally selective kappa opioid receptor agonists of the invention can be peptides, such as those containing D-amino acids instead of L-amino acids, and which optionally can have little to no sequence homology with known mammalian endogenous opioid peptides, e.g., the enkephalins, endorphins, and dynorphins. A peripherally selective kappa opioid receptor agonist can comprise a tetrapeptide D-amino acid sequence. Peptides that are encompassed by the criteria of the invention are any of the known mammalian endogenous opioid peptides, e.g., as identified in Akil et al (1984), such as dynorphin A(1-17), including naturally occurring, processed forms of these peptides, e.g., dynorphin A(1-13) and dynorphin A (1-8).

The invention, among other things, relates to the use of peripherally selective kappa opioid receptor agonists alone or in conjunction with lactational enhancers, elevators, or stabilizers for the treatment of lactation failure, or inadequate or insufficient lactation in a subject.

The invention also relates to the use of peripherally selective kappa opioid agonists, alone or in conjunction with lactational enhancers elevators, or stabilizers for the manufacture of a medicament in treatment of lactation failure or inadequate or insufficient lactation in a subject.

Lactational enhancers, elevators, or stabilizers can be chosen from among D2 dopamine receptor antagonists, mu opioid receptor agonists, prolactin, or oxytocin, for example.

The invention further relates to a method for the treatment of lactation failure, or inadequate or insufficient lactation in a subject, characterized in that a peripherally selective kappa opioid receptor agonist, alone or in conjunction with a lactational enhancer, elevator, or stabilizer is administered to a female subject. Non-limiting administration methods include subcutaneous, intravenous, intramuscular, nasal, oral or transdermal administration.

The invention moreover relates to a composition comprising peripherally selective kappa opioid receptor agonist in conjunction with a lactational enhancer, elevators, or stabilizers, optionally including a pharmaceutically acceptable carrier. These and other compositions set forth herein can be used in methods for the treatment of lactation failure, or inadequate or insufficient lactation in a subject, in accordance with the invention, as well as a method for the manufacture of these compositions.

By lactation failure is here meant both when a female has no or insufficient amount of milk or is at risk for none or insufficient amount of milk.

Lactation can be promoted and, therefore, lactation failure, or inadequate or insufficient lactation in a subject, methods are provided in the following situations;

i) Normalize lactation volumes in women with lactational failure;
ii) Maintain/enhance, increase lactation in females of premature babies who are being cared for in a neonatal unit;
iii) Enhance lactational performance in females with twins and triplets;

iv) Promote and prolong (frequency or duration) lactation in females with offspring at risk of developing lactose intolerance or other milk allergies if formula milk was used;
v) Promote/prolong lactation in females where adverse hygiene conditions would make the use of formula undesirable;
vi) Enhance, increase or stabilize lactation in females where suckling frequency is diminished during part of the day, e.g. working mothers;
vii) To treat females prophylactically if they are at risk for having an insufficient or inadequate amount of milk production.

Certain embodiments of the invention involve peptides, optionally tetrapeptides containing four D-isomer amino acid residues, which bind to kappa, opioid receptor receptors, which do not substantially cross the blood brain barrier and enter the brain, which exhibit high affinity for the kappa opioid receptor versus the mu opioid receptor, which have high potency and efficacy, and can exhibit a relative long duration of action in vivo.

It is an object herein to provide peripherally selective kappa opioid receptor agonists for systemic application that have tolerable, minimal or few if any CNS or diuretic effects at dosages that are sufficient to elevate, increase or stabilize prolactin and thereby produce a benefit, such as increased lactation or prevent significant reductions, or decreases in lactation, in a subject in need thereof.

Mammals are defined herein as all animals, including humans, primates, and ungulates, for which the females of the species have mammary glands and produce milk.

As used herein, a "dairy animal" refers to a milk producing animal. In certain embodiments, the dairy animal produces large volumes of milk and has a long period of lactation, e.g., cows or goats.

The term "pharmaceutically acceptable composition" refers to compositions which comprise a therapeutically effective amount of peripherally selective kappa opioid receptor agonist, formulated together with one or more pharmaceutically acceptable carrier(s).

As used herein, the term "formulation" refers to a composition in solid, e.g., powder, or liquid form, which includes a peripherally selective kappa opioid receptor agonist. Formulations can provide therapeutic benefits. These formulations may contain a preservative to prevent growth of microorganisms.

By "therapeutically effective" amount is meant a tolerable (e.g., does not produce a severe side effect, which can be relatively, substantially, or completely nontoxic) amount of an active agent to provide the desired therapeutic effect.

By "transdermal" drug delivery is meant administration of a drug to the skin surface of an individual so that the drug passes through the skin tissue and into the individual's blood stream, thereby providing a systemic effect. The term "transdermal" is intended to include "transmucosal" drug administration, i.e., administration of a drug to the mucosal (e.g., sublingual, buccal, vaginal, rectal) surface of an individual so that the drug passes through the mucosal tissue and into the individual's blood stream.

The term "body surface" is used to refer to skin or mucosal tissue.

By "predetermined area" of skin or mucosal tissue, which refers to the area of skin or mucosal tissue through which a drug enhancer formulation is delivered, is intended a defined area of intact unbroken living skin or mucosal tissue. That area will usually be in the range of about 5 cm$^2$ to about 200 cm$^2$, more usually in the range of about 5 cm$^2$ to about 100 cm$^2$, typically in the range of about 20 cm$^2$ to about 60 cm$^2$.

However, it will be appreciated by those skilled in the art of drug delivery that the area of skin or mucosal tissue through which drug is administered may vary significantly, depending on patch configuration, dose, and the like.

"Penetration enhancement" or "permeation enhancement" as used herein relates to an increase in the permeability of the skin or mucosal tissue to a selected pharmacologically active agent, i.e., so that the rate at which the agent permeates therethrough (i.e., the "flux" of the agent through the body surface) is increased relative to the rate that would be obtained in the absence of permeation enhancement. The enhanced permeation effected through the use of such enhancers can be observed by measuring the rate of diffusion of drug through animal or human skin using, for example a Franz diffusion apparatus as known in the art and as employed in the Examples herein.

An "effective amount" or "an effective permeation enhancing amount" of a permeation enhancer refers to a nontoxic, nondamaging but sufficient amount of the enhancer composition to provide the desired increase in skin permeability and, correspondingly, the desired depth of penetration, rate of administration, and amount of drug delivered.

A genus of peptides has been discovered which exhibit high selectivity for the kappa opioid receptor and relative long duration of in vivo action and which can exhibit reduced or substantially little if any significant brain penetration. These peptides include sequences in which a sequence of four D-isomer amino acids having a C-terminus is either a mono or disubstituted amide. These compounds have the following general formula:

HXaa$_1$-Xaa$_2$-Xaa$_3$-Xaa$_4$-substituted amide wherein Xaa$_1$ is (A)D-Phe, (C$^{alpha}$ Me)D-Phe, D-Tyr, D-Tic or D-Ala(cyclopentyl or thienyl), with A being H, NO$_2$, F, Cl or CH$_3$; Xaa$_2$ is (A')D-Phe, D-1Nal, D-2Nal, D-Tyr or D-Trp, with A' being A or 3,4Cl$_2$, Xaa$_3$ is D-Nle, (B)D-Leu, D-Hle, D-Met, D'-Val, D-Phe or D-Ala(cyclopentyl) with B being H or C$^{alpha}$ Me; Xaa$_4$ is D-Arg, D-Har, D-nArg, D-Lys, D-Lys (Ipr), D-Arg(Et$_2$), D-Har(Et$_2$), D-Amf(G), D-Dbu, (B)D-Orn or D-Orn(Ipr), and with G being H or amidino. Non-limiting amides include ethylamide, morpholinylamide, 4-picolylamide, piperazineamide, propylamide, cyclopropylamide and diethylamide.

The invention also provides a method of treating a mammal in need of elevated prolactin by increasing levels of serum prolactin of said mammal, comprising administering to said mammal an amount of a peripherally selective kappa opioid receptor agonist or a salt thereof or a pro-drug thereof effective to treat the mammal. In certain embodiments, the method increases or stabilizes levels of serum prolactin to greater than 25, 50, 75, 100, 125, 150, 175, or 200 ng/ml serum in the mammal. In other embodiments the method the peripherally selective kappa opioid receptor agonist or salt thereof or prodrug thereof effective to treat the mammal is a peptide, or ionizes or is metabolized to form a peptide. The peptide can comprise a pentapeptide or tetrapeptide, which can include a sequence of four D-isomer amino acids having a C-terminus that is either a mono- or di-substituted amide. In certain embodiments the peptide has a binding affinity for the kappa opioid receptor that is greater than its binding affinity for non-kappa opioid receptors. In particular embodiments the peptide has a binding affinity for the kappa opioid receptor at least 1,000 times greater than its binding affinity for the mu opioid receptor. In some of these particular embodiments the peptide has a binding affinity for the kappa opioid receptor at least 1,000 times greater than its binding affinity for the mu opioid receptor and in addition has an $ED_{50}$ for elevating prolactin of about 0.5 mg/kg or less.

Particular compounds useful in the methods of the present invention include the compound having the formula:

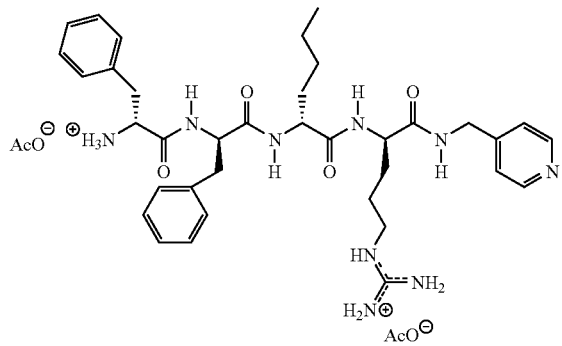

H-D-Phe-D-Phe-D-Nle-D-Arg-NH-4-picolyl, or a picolyl N-oxide thereof, optionally excluding or including an acetate counterion.

Another particular compound useful in the methods of the present invention is the compound having the formula:

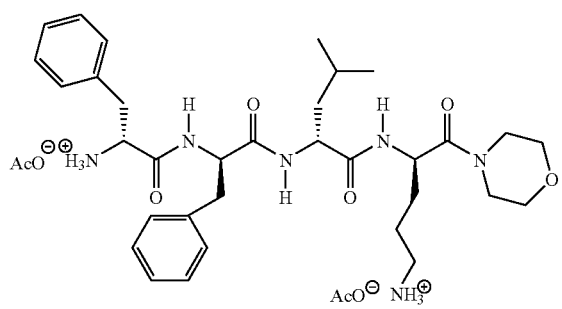

H-D-Phe-D-Phe-D-Leu-D-Orn-Morpholinyl, optionally excluding or including an acetate counterion.

BRIEF DESCRIPTION OF THE FIGURES

FIG. 1 is a graph showing the Arithmetic Mean Changes from Baseline (Pre dose) in Serum Prolactin Concentrations Following a 1 hour IV Infusion of CR665 at various dosages in Male Subjects (Part A).

FIG. 2 is a graph showing the Arithmetic Mean Changes from Baseline (Pre dose) in Serum Prolactin Concentrations Following a 1 hour IV Infusion of CR665 in Female Subjects (Part A).

FIG. 3 is a graph showing the Arithmetic Mean Changes from Baseline (Pre dose) in Serum Prolactin Concentrations Following a 5 minute IV. Infusion of CR665 in Male Subjects (Part B).

FIG. 4 is a graph showing the Geometric Mean Plasma Concentrations of CR665 Following a 1 hour IV Infusion of CR665 in Male Subjects (Part A) (Linear Scale).

FIG. 5 is a graph showing the Geometric Mean Plasma Concentrations of CR665 Following a 1 hour IV Infusion of CR665 in Male Subjects (Part A) (Semi logarithmic Scale).

FIG. 6 is a graph showing the Geometric Mean $AUC0$ for CR665 Versus Dose Level Following a 1 hour IV Infusion of CR665 in Male Subjects (Part A).

FIG. 7 is a graph showing the Geometric Mean Plasma Concentrations of CR665 Following a 1 hour IV Infusion of 0.24 mg/kg CR665 in Female Subjects (Part A) (Linear Scale).

FIG. 8 is a graph showing the Geometric Mean Plasma Concentrations of CR665 Following a 1 hour IV Infusion of 0.24 mg/kg CR665 in Female Subjects (Part A) (Semi logarithmic Scale).

FIG. 9 is a graph showing the Arithmetic Mean ($\pm$SD) Plasma Concentrations of CR665 Following a 1-hour IV Infusion of 0.24 mg/kg CR665 in Male and Female Subjects (Part A) (Linear Scale).

FIG. 10 is a graph showing the Geometric Mean Plasma Concentrations of CR665 Following a 5-minute IV Infusion of CR665 in Male and Female Subjects (Part B) (Linear Scale).

FIG. 11 is a graph showing the Geometric Mean Plasma Concentrations of CR665 Following a 5-minute IV Infusion of CR665 in Male and Female Subjects (Part B) (Semi logarithmic Scale).

FIG. 12 is a graph showing the Geometric Mean $AUC_{(0\ to\ infinity)}$ for CR665 Versus Dose Level Following a 5-minute IV Infusion of CR665 in Male Subjects (Part B).

FIG. 13 is a graph showing the Relationship Between AUC0 12 h of Changes from Baseline in Serum Prolactin and $AUC_{(0\ to\ infinity)}$ of CR665 over the 0.015 to 0.36 mg/kg Dose Range in Male Subjects (Part A).

FIG. 14 is a graph showing the Relationship Between Cmax of Changes from Baseline in Serum Prolactin and Cmax of CR665 over the 0.015 to 0.36 mg/kg Dose. Range in Male Subjects (Part A).

DETAILED DESCRIPTION

The nomenclature used to define the peptides is specified by Schroder & Lubke, The Peptides, Academic Press, 1965, wherein, in accordance with conventional representation, the N-terminus appears to the left and the C-terminus to the right. Where an amino acid residue has isomeric forms, it is the L-isomer form of the amino acid that is being represented herein unless otherwise indicated.

The invention provides methods, compositions, or dosage forms that employ and/or contain compounds, such as peptides, that are selective for kappa opioid receptor and not only exhibit a strong affinity for the kappa opioid receptor but exhibit, optionally, long duration of in vivo prolactin elevating activity in the absence of a severe or significant side effect, such as CNS side effects or diuresis. Exemplary kappa selective opioid receptor compounds (e.g., agonists) have a Ki against a mammalian kappa opioid receptor, such as a human kappa opioid receptor, of less than 1000 nM, or less than 100 nM or less than 10 nM, or less than 1 nM, optionally having a selectivity for kappa opioid receptors over other mammalian opioid receptor subtypes greater than 100, or greater than 1,000 or greater than 10,000 times greater affinity, measurable in vitro by the ratio of their IC50 or Ki values against the mammalian, e.g., human mu and delta opioid receptors, respectively. Kappa opioid receptor agonists can exhibit both a lack of significant brain penetration and a prolonged duration of in vivo activity. Therefore, in addition to the above mentioned kappa opioid receptor affinity and selectivity, compounds also include those that exhibit no significant brain penetration while preserving substantial activity for measurable or detectable period of time, for example, at least about one hour, at least about two hours, for three hours or longer (e.g., 4, 5, 6, 12, 24, 48 hours or days, or longer).

In certain embodiments, the method of the invention can be practiced using a peripherally selective kappa opioid receptor agonist, which when administered peripherally, is effective to increase or stabilize levels of prolactin without substantially crossing the blood-brain barrier of the subject. In other embodiments, the amount of the peripherally selective kappa opioid receptor agonist administered is an amount effective to increase or stabilize levels of prolactin without causing a severe side effect in the subject. Alternatively, the amount of the peripherally selective kappa opioid receptor agonist administered is an amount effective to increase or stabilize levels of prolactin with minor or tolerable side effects in the subject. Side effects can include a neuropsychiatric side effect (such as but not limited to dysphoria or hallucinations), diuresis or sedation.

In some embodiments, according to the method of the invention for elevating levels of serum prolactin in a mammal, the administered dose of the peripherally selective kappa opioid receptor agonist is between about 1 microgram/kg of body weight to about 100 milligrams/kg of body weight of said mammal per hour, or per day, or per week or per month. The prolactin levels can be elevated to greater than 10, 15, 20, 25, 50, 75, 100, 125, 150, 175, or 200 ng/ml serum above the baseline level of serum prolactin.

In some embodiments, the method of the invention for treating insufficient or inadequate lactation in a mammal, includes administering, separately or in combination an amount of a peripherally selective kappa opioid receptor agonist or a salt thereof or a pro-drug thereof, and an amount of prolactin effective to treat insufficient or inadequate lactation in the mammal. In other embodiments, the invention provides a method for treating insufficient or inadequate lactation. The method includes administering an amount of a peripherally selective kappa opioid receptor agonist or a salt thereof or a pro-drug thereof, to a mammal, separately or in combination, with (1) another prolactin-elevating agent, (2) prolactin, or (3) a non-drug therapy, the method effective to treat insufficient or inadequate lactation in the mammal. In still other embodiments, the invention provides a method for treating insufficient or inadequate lactation in a mammal. The method includes administering separately or in combination 1) a peripherally selective kappa opioid receptor agonist or a salt thereof or a pro-drug thereof, and; 2) another prolactin-elevating agent, said administration in an amount effective for treating insufficient or inadequate lactation in the mammal.

In other embodiments, the invention provides a method of for treating a mammal exhibiting insufficient or inadequate milk production or at risk of insufficient or inadequate milk production. The method includes administering to said mammal an amount of a peripherally selective kappa opioid receptor agonist or salt thereof or prodrug thereof effective to treat the mammal. The peripherally selective kappa opioid receptor agonist or salt thereof or prodrug thereof can include a peptide, or can ionize or metabolize to form a peptide. The peptide can include a tetrapeptide or a pentapeptide.

In particular embodiments, the prolactin-elevating agent useful in the methods of the present invention can be administered with a mu opioid receptor agonist selected from the group consisting of (i) morphine, (ii) hydromorphone, (iii) oxymorphone, (iv) levorphanol; (v) methadone, (vi) codeine, (vii) hydrocodone, (viii) oxycodone, (ix) morphine 6 glucuronide, (x) tramadol, (xi) meperidine, (xii) diphenoxylate, (xiii) loperamide, (xiv) fentanyl, (xv) sufentanil, (xvi) alfentanil, (xvii) remifentanil, (xviii) levomethadyl and (xviv) propoxyphene.

In certain embodiments of the method, the prolactin-elevating agent can be a peptide having a binding affinity for the peripheral kappa opioid receptor that is greater than its binding affinity for non-peripheral kappa opioid receptor. Alternatively, the peptide can have a binding affinity for the peripheral kappa opioid receptor that is 10 times greater, 100 times greater, 1,000 times greater, or more than its binding affinity for a non-peripheral kappa opioid receptor. For instance the peptide can have a binding affinity for the kappa opioid receptor which is at least 1,000 times greater than its binding affinity for the mu opioid receptor. In certain embodiments, the peptide has a binding affinity for the kappa opioid receptor which is at least 1,000 times greater than its binding affinity for the mu opioid receptor and an $ED_{50}$ for elevating prolactin of about 0.5 mg/kg or less.

In a particular embodiment, the invention provides a method of treating a mammal in need of elevated or stabilized prolactin levels, wherein the method includes administering to said mammal an amount of a peripherally selective kappa opioid receptor agonist or a salt thereof or a pro-drug thereof, in conjunction with an amount of an additional prolactin elevating compound, effective to treat the mammal. The additional prolactin elevating compound can include a D2 dopamine receptor antagonist or mu opioid receptor agonist.

In one embodiment, the D2 dopamine receptor agonist is selected from the group consisting of (i) domperidone, (ii) metoclopramide, (iii) levosulpiride, (iv) sulpiride, (v) thiethylperazine, (vi) ziprasidone, (vii) zotepine, (viii) clozapine, (ix) chlorpromazine, (x) acetophenazine, (xi) carphenazine (xii) chlorprothixene, (xiii) fluphenazine, (xiv) loxapine, (xv) mesoridazine, (xvi) molindone, (xvii) perphenazine, (xviii) pimozide, (xviv) piperacetazine, (xx) prochlorperazine, (xxi) thioridazine, (xxii) thiothixene, (xxiii) trifluoperazine, (xxiv) triflupromazine, (xxv) pipamperone, (xxvi) amperozide, (xxvii) quetiapine, (xxviii) melperone, (xxix) remoxipride, (xxx) haloperidol, (xxxi) rispiridone, (xxxii) olanzepine, (xxxiii) sertindole, and (xxxiv) prochlorperazine.

In another embodiment the mu opioid receptor agonist is selected from the group consisting of (i) morphine, (ii) hydromorphone, (iii) oxymorphone, (iv) levorphanol, (v) methadone, (vi) codeine, (vii) hydrocodone, (viii) oxycodone, (ix) morphine-6-glucuronide, (x) tramadol, (xi) meperidine, (xii) diphenoxylate, (xiii) loperamide, (xiv) fentanyl, (xv) sufentanil, (xvi) alfentanil, (xvii) remifentanil, (xviii) levomethadyl, and (xviv) propoxyphene.

As used herein, "prolactin elevating activity" refers to the pharmacological activity of a compound If it causes an elevation in circulating plasma or serum levels of prolactin in a subject. A "prolactin increasing activity" refers to a compound that causes a measurable or detectable, transient or longer term increase in circulating plasma or serum levels of prolactin in a subject. A "prolactin stabilizing activity" refers to a compound that causes a measurable or detectable, transient or longer term, stabilization in circulating plasma or serum levels of prolactin in a subject, e.g., prevents or inhibits a reduction in prolactin levels, maintains a particular level of prolactin for a measurable period of time, prevents or inhibits a reduction in prolactin levels below a certain amount (e.g., below 200, 175, 150, 125, 100, 75, 50, 25 ng/ml serum), etc.

As used herein, "functional hypoprolactinemia" refers to a condition in which a subject has insufficient or inadequate levels of circulating prolactin required to initiate, maintain or enhance a physiological function, e.g. lactation. The level of circulating prolactin required for a given physiological function will vary, as is known in the art, depending upon the function and the gender and physiological or pathophysiological status of the subject. Thus, for example, a normal pre pregnancy baseline level of circulating prolactin would be insufficient to sustain lactation after delivery. Under these circumstances, the failure of lactation in a post pregnant female with this level of prolactin would be characterized as a functional hypoprolactinemia, even though the circulating level of prolactin would be normal for a non lactating female.

As used herein, "CNS side effect" refers to a clinically significant side effect of a compound in which the symptoms are psychiatric or neurological, e.g., visual or auditory hallucinations, delusions, impaired intellectual functioning, or impaired control of voluntary movements.

As used herein, the term "subject" is intended to include human and non human mammals. Subjects include a person, e.g., a patient, in need of elevated, increased or stabilized levels of prolactin, e.g., a person in need of stimulation of lactation, e.g., a female (mother). The term "mammals" includes humans and all non human mammals, such as non human primates, ungulates and ruminants.

As used herein, "effective amount" or "sufficient amount" refers to an amount of a compound as described herein that may be therapeutically effective to inhibit, prevent or treat a symptom of a particular disease, disorder, condition, or side effect. Such diseases, disorders, conditions, and side effects include those conditions associated with insufficient, or inadequate circulating levels of prolactin, wherein the treatment comprises elevating, increasing or stabilizing circulating levels of prolactin by contacting cells, tissues or receptors with compounds as set forth herein. Thus, for example, an "effective amount", when used in connection with lactational insufficiency or inadequacy, for example, refers to an amount of a compound required for treatment and/or prevention of this condition. An "effective amount", when used in connection with functional hypoprolactinemia, refers to the treatment and/or prevention of one or more symptoms, diseases, disorders, and conditions associated with circulating levels of prolactin that are undesirably low, for example, to optimally sustain a physiological function.

As used herein, "pharmaceutically acceptable" refers to compounds, materials, compositions, and/or dosage forms which are, within the scope of sound medical judgment, suitable for contact with the tissues of human beings and animals without severe toxicity, irritation, allergic response, or other complications commensurate with a reasonable benefit/risk ratio.

As used herein, "in combination with", "combination therapy" and "combination products" refer, in certain embodiments, to the concurrent administration to a patient of a peripherally selective kappa opioid receptor agonist of the invention and either or both of prolactin and a compound with prolactin elevating, increasing or stabilizing activity but lacking peripherally selective kappa opioid receptor agonist activity, e.g., a D2 dopamine receptor antagonist, e.g., domperidone. When administered in combination, each component may be administered at the same time or sequentially in any order at different points in time. Thus, each component may be administered separately but sufficiently closely in time so as to provide a desired therapeutic effect.

As used herein, a "D2 dopamine receptor antagonist" refers to compounds with a binding affinity ($K_D$ or $K_i$) for a mammalian D2 dopamine receptor of less than 10 micromolar, regardless of binding affinity for other receptors. Where there is ambiguity or an absence of useful information regarding whether the binding affinity of a compound for a mammalian D2 dopamine receptor meets this definition, data from in vitro or in vivo functional studies, as are commonly employed by those with skill in the art, can be used to determine whether a compound is a functional antagonist of a mammalian D2 dopamine receptor.

As used herein, "mu opioid receptor agonist" refers to compounds with a binding affinity ($K_D$ or $K_i$) for a mammalian mu opioid receptor of less than 10 micromolar, regardless of binding affinity for other receptors. Where there is ambiguity or an absence of useful information regarding whether the binding affinity of a compound for a mammalian mu opioid receptor meets this definition, data from in vitro or in vivo functional studies, as are commonly employed by those with skill in the art, can be used to determine whether a compound is a functional agonist of a mammalian mu opioid receptor.

As used herein, "dosage unit" refers to a physically discrete unit suited as unitary dosages for a particular individual or condition to be treated. Each unit may contain a predetermined quantity of active compound(s) calculated to produce the desired therapeutic effect(s), optionally in association with a pharmaceutical carrier. The specification for the dosage unit forms may be dictated by (a) the unique characteristics of the active compound(s) and the particular therapeutic effect(s) to be achieved, and (b) the limitations inherent in the art of compounding such active compound(s).

As used herein, "pharmaceutically acceptable salts" refer to derivatives of compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non toxic salts or the quaternary ammonium salts of the parent compound formed, for example, from non toxic inorganic or organic acids. For example, such conventional non toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2 acetoxybenzoic, fumaric, toluenesulfonic, methanesulfonic, ethane disulfonic, oxalic, isethionic, and the like. These physiologically acceptable salts are prepared by methods known in the art, e.g., by dissolving the free amine bases with an excess of the acid in aqueous alcohol, or neutralizing a free carboxylic acid with an alkali metal base such as a hydroxide, or with an amine.

Compounds described herein, can be used or prepared in alternate forms. For example, many amino containing compounds can be used or prepared as an acid addition salt. Often such salts improve isolation and handling properties of the compound. For example, depending on the reagents, reaction conditions and the like, compounds as described herein can be used or prepared, for example, as their hydrochloride or tosylate salts. Isomorphic crystalline forms, all chiral and racemic forms, N-oxide, hydrates, solvates, and acid salt hydrates, are also contemplated to be within the scope of the present invention.

Certain acidic or basic compounds of the present invention may exist as zwitterions. All forms of the compounds, including free acid, free base and zwitterions, are contemplated to be within the scope of the present invention. It is well known in the art that compounds containing both amino and carboxyl groups often exist in equilibrium with their zwitterionic forms. Thus, any of the compounds described herein throughout that contain, for example, both amino and carboxyl groups, also include reference to their corresponding zwitterions.

PHARMACEUTICAL COMPOSITIONS

A peripherally selective kappa opioid receptor agonist of the invention can be incorporated into a pharmaceutical composition to ameliorate functional hypoprolactinemia in a subject, e.g., a subject presenting with a deficiency, inadequacy or insufficiency in lactation associated with insufficient or inadequate plasma levels of prolactin. The compositions should contain an effective amount of a peripherally selective kappa opioid receptor agonist, in a pharmaceutically acceptable carrier.

The pharmaceutical carrier can be any compatible, non toxic substance suitable to deliver the peripherally selective kappa opioid receptor agonist to the subject. Sterile water, alcohol, fats, waxes, and inert solids may be used as the carrier. Pharmaceutically acceptable adjuvants, buffering agents, dispersing agents, and the like, may also be incorporated into the pharmaceutical compositions. The concentration of peripherally selective kappa opioid receptor agonist or other active agent in the pharmaceutical composition can vary widely, i.e., from less than about 0.01% by weight, usually being at least about 1% weight to as much as 50% by weight or more.

For oral administration, an active ingredient can be administered in solid dosage forms, such as capsules, tablets, and powders, or in liquid dosage forms, such as elixirs, syrups, and suspensions. Active component(s) can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate and the like. Examples of additional inactive ingredients that may be added to provide desirable color, taste, stability, buffering capacity, dispersion or other known desirable features are red iron oxide, silica gel, sodium lauryl sulfate, titanium dioxide, edible white ink and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract. Liquid dosage forms for oral administration can contain coloring and flavoring to increase patient acceptance. To facilitate drug stability and absorption, peptides of the invention can be released from a capsule after passing through the harsh proteolytic environment of the stomach. Methods for enhancing peptide stability and absorption after oral administration are well known in the art (e.g., Mahato R I. Emerging trends in oral delivery of peptide and protein drugs. *Critical Reviews in Therapeutic Drug Carrier Systems.* 20:153-214, 2003). In addition, oral delivery of compounds of the invention can be optimized through the use of remote controlled capsules as disclosed by Wilding and Prior in *Critical Reviews in Therapeutic Drug Carrier Systems* 20:405-431 (2003).

For nasal administration, the peripherally selective kappa opioid receptor agonists can be formulated as aerosols. The term "aerosol" includes any gas-borne suspended phase of the compounds of the instant invention which is capable of being inhaled into the bronchioles or nasal passages. Specifically, aerosol includes a gas-borne suspension of droplets of the compounds of the instant invention, as may be produced in a metered dose inhaler or nebulizer, or in a mist sprayer. Aerosol also includes a dry powder composition of a compound of the instant invention suspended in air or other carrier gas, which may be delivered by insufflation from an inhaler device, for example. See Ganderton & Jones, Drug Delivery to the Respiratory Tract, Ellis Horwood (1987); Gonda (1990) *Critical Reviews in Therapeutic Drug Carrier Systems* 6:273-313; and Raeburn et al. (1992) *J. Pharmacol. Toxicol. Methods* 27:143-159.

Parenteral administration of the formulations of the present invention includes intravenous, subcutaneous, intramuscular and transdermal administrations.

Preparations for parenteral administration include sterile solutions ready for injection, sterile dry soluble products ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous, and thereby formulated for delivery by injection, infusion, or using implantable pumps. For intravenous, subcutaneous, and intramuscular administration, useful formulations of the invention include microcapsule preparations with controlled release properties (R. Pwar et al. Protein and peptide parenteral controlled delivery. *Expert Opin Biol Ther.* 4(8): 1203-12, 2004) or encapsulation in liposomes, with an exemplary form being polyethylene coated liposomes, which are known in the art to have an extended circulation time in the vasculature (e.g. Koppal, T. "Drug delivery technologies are right on target", *Drug Discov. Dev.* 6, 49-50, 2003).

Preparations for transdermal delivery are incorporated into a device suitable for said delivery, said device utilizing, e.g., iontophoresis (Kalia Y N et al. Iontophoretic drug delivery. *Adv Drug Deliv Rev.* 56:619-58, 2004) or a dermis penetrating surface (Prausnitz M R. Microneedles for transdermal drug delivery. *Adv Drug Deliv Rev.* 56:581-7, 2004), such as are known in the art to be useful for improving the transdermal delivery of drugs. An electrotransport device and methods of operating same are disclosed in U.S. Pat. No. 6,718,201. Methods for the use of iontophoresis to promote transdermal delivery of peptides are disclosed in U.S. Pat. Nos. 6,313,092 and 6,743,432. Herein the terms "electrotransport", "iontophoresis", and "ion tophoretic" are used to refer to the delivery through a body surface (e.g., skin or mucosa) of one or more pharmaceutically active compounds by means of an applied electromotive force to an agent containing reservoir. The compound may be delivered by electromigration, electroporation, electroosmosis or any combination thereof. Electroosmosis has also been referred to as electrohydrokinesis, electro convection, and electrically induced osmosis. In general, electroosmosis of a compound into a tissue results from the migration of solvent in which the compound is contained, as a result of the application of electromotive force to the therapeutic species reservoir, i.e., solvent flow induced by electromigration of other ionic species. During the electrotransport process, certain modifications or alterations of the skin may occur such as the formation of transiently existing pores in the skin, also referred to as "electroporation." Any electrically assisted transport of species enhanced by modifications or alterations to the body surface (e.g., formation of pores in the skin) are also included in the term "electrotransport" as used herein. Thus, as used herein, applied to the compounds of the instant invention, the terms "electrotransport", "iontophoresis" and "iontophoretic" refer to (1) the delivery of charged agents by electromigration, (2) the delivery of uncharged agents by the process of electroosmosis, (3) the delivery of charged or uncharged agents by electroporation, (4) the delivery of charged agents by the combined processes of electromigration and electroosmosis, and/or (5) the delivery of a mixture of charged and uncharged agents by the combined processes of electromigration and electroosmosis. Electrotransport devices generally employ two electrodes, both of which are positioned in close electrical contact with some portion of the skin of the body. One electrode, called the active or donor electrode, is the electrode from which the therapeutic agent is delivered into the body. The other electrode, called the counter or return electrode, serves to close the electrical circuit through the body. In conjunction with the patient's skin, the circuit is completed by connection of the electrodes to a source of electrical energy, e.g., a battery, and usually to circuitry capable of controlling current passing through the device.

Depending upon the electrical charge of the compound to be delivered transdermally, either the anode or cathode may be the active or donor electrode. Thus, if the compound to be transported is positively charged, e.g., the compound exemplified in Example 1 herein, then the positive electrode (the anode) will be the active electrode and the negative electrode (the cathode) will serve as the counter electrode, completing the circuit. However, if the compound to be delivered is negatively charged, then the cathodic electrode will be the active electrode and the anodic electrode will be the counter electrode. Electrotransport devices additionally require a reservoir or source of the therapeutic agent that is to be delivered into the body. Such drug reservoirs are connected to the anode or the cathode of the electrotransport device to provide a fixed or renewable source of one or more desired species or agents. Each electrode assembly is comprised of an electrically conductive electrode in ion-transmitting relation with an ionically conductive liquid reservoir which in use is placed in contact with the patient's skin. Gel reservoirs such as those described in Webster (U.S. Pat. No. 4,383,529) are one form of reservoir since hydrated gels are easier to handle and manufacture than liquid-filled containers. Water is one liquid solvent that can be used in such reservoirs, in part because the salts of the peptide compounds of the invention are water soluble and in part because water is non-irritating to the skin, thereby enabling prolonged contact between the hydrogel reservoir and the skin. Examples of reservoirs and sources include a pouch as described in U.S. Pat. No. 4,250,878, a pre-formed gel body as disclosed in U.S. Pat. No. 4,382,529, and a glass or plastic container holding a liquid solution of the drug, as disclosed in the figures of U.S. Pat. No. 4,722,726. For electrotransport, compounds (e.g., peptides) the invention can be formulated with flux enhancers such as ionic surfactants (e.g., U.S. Pat. No. 4,722,726) or cosolvents other than water (e.g., European Patent Application 278,473). Alternatively the outer layer (i.e., the stratum corneum) of the skin can be mechanically disrupted prior to electrotransport delivery therethrough (e.g., U.S. Pat. No. 5,250,023).

Peripherally selective kappa opioid receptor agonists that are well suited for electrotransport can be selected by measuring their electrotransport flux through the body surface (e.g., the skin or mucosa), e.g., as compared to a standardized test peptide with known electrotransport flux characteristics, e.g. thyrotropin releasing hormone (R. Burnette et al. *J. Pharm. Sci.* (1986) 75:738) or vasopressin (Nair et al. *Pharmacol Res.* 48:175-82, 2003). Transdermal electrotransport flux can be determined using a number of in vivo or in vitro methods well known in the art. In vitro methods include clamping a piece of skin of an appropriate mammal (e.g., human cadaver skin) between the donor and receptor compartments of an electrotransport flux cell, with the stratum corneum side of the skin piece facing the donor compartment. A liquid solution or gel containing the drug to be delivered is placed in contact with the stratum corneum, and electric current is applied to electrodes, one electrode in each compartment. The transdermal flux is calculated by sampling the amount of drug in the receptor compartment. Two successful models used to optimize transdermal electrotransport drug delivery are the isolated pig skin flap model (Heit M C et al. Transdermal iontophoretic peptide delivery: in vitro and in vivo studies with luteinizing hormone releasing hormone. *J. Pharm. Sci.* 82:240 3, 1993), and the use of isolated hairless skin from hairless rodents or guinea pigs, for example. See Hadzija B W et al. Effect of freezing on iontophoretic transport through hairless rat skin. *J. Pharm. Pharmacol.* 44, 387 390, 1992. Compounds of the invention for transdermal iontophoretic delivery can have one, or typically, two charged nitrogens, to facilitate their delivery.

The scope of the present invention also includes methods of treating a mammal in need of elevated prolactin wherein the peripherally selective kappa opioid receptor agonist or a salt thereof or a pro-drug thereof is administered transdermally, for instance and without limitation, by an electrotransport device. The electrotransport device can, in some embodiments, deliver the peripherally selective kappa opioid receptor agonist or a salt thereof or a pro-drug thereof through a body surface.

Other useful transdermal delivery devices employ high velocity delivery under pressure to achieve skin penetration without the use of a needle. Transdermal delivery can be improved, as is known in the art, by the use of chemical enhancers, sometimes referred to in the art as "permeation enhancers", i.e., compounds that are administered along with the drug (or in some cases used to pretreat the skin, prior to drug administration) in order to increase the permeability of the stratum corneum, and thereby provide for enhanced penetration of the drug through the skin. Chemical penetration enhancers are compounds that are innocuous and serve merely to facilitate diffusion of the drug through the stratum corneum, whether by passive diffusion or an energy driven process such as electrotransport. See, for example, Meidan V M et al. Enhanced iontophoretic delivery of buspirone hydrochloride across human skin using-chemical enhancers. *Int. J. Pharm.* 264:73-83, 2003.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations must be added to parenteral preparations packaged in multiple dose containers which include phenols or cresols, mercurials, benzyl alcohol, chlorobutanol, methyl and propyl p hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcelluose, hydroxypropyl methylcellulose and polyvinylpyrrolidone. Emulsifying agents include Polysorbate 80 (Tween 80). A sequestering or chelating agent of metal ions includes EDTA. Pharmaceutical carriers also include ethyl alcohol, polyethylene glycol and propylene glycol for water miscible vehicles and sodium hydroxide, hydrochloric acid, citric acid or lactic acid for pH adjustment.

Typically a therapeutically effective amount of a peripherally selective kappa opioid receptor agonist is at least about 0.01% w/w up to about 50% w/w or more, or more than 0.1% w/w of the active compound. The active ingredient may be administered at once, or may be divided into a number of smaller doses to be administered at intervals of time, or as a controlled release formulation. The term "controlled release formulation" encompasses formulations that allow the continuous delivery of a peripherally selective kappa opioid receptor agonist to a subject over a period of time, for example, several days to weeks. Such formulations may administered subcutaneously or intramuscularly and allow for the continual steady state release of a predetermined amount of compound in the subject over time. The controlled release formulation of peripherally selective kappa opioid receptor agonist may be, for example, a formulation of drug containing polymeric microcapsules, such as those described in U.S. Pat. Nos. 4,677,191 and 4,728,721, incorporated herein by reference. The concentration of the pharmaceutically active compound is adjusted so that administration provides an effective amount to produce a desired effect. The exact dose depends on the age, weight and condition of the patient or animal, as is known in the art. For any particular subject, specific dosage regimens can be adjusted over time according to the individual need and the professional judgment of the person administering or supervising the administration of the formulations. Thus, the concentration ranges set forth herein are exemplary only and are not intended to limit the scope or practice of the claimed invention.

The unit dose parenteral preparations include packaging in an ampoule or a syringe with a needle.

All preparations for parenteral administration are typically sterile, as is known and practiced in the art.

Illustratively, intravenous infusion of a sterile aqueous buffered solution containing an active compound is an effective mode of administration. Another embodiment is a sterile aqueous or oily solution or suspension containing an active material injected as necessary to produce the desired pharmacological effect.

Compositions and methods of the invention can be delivered or administered intravenously, transdermally, intranasally, subcutaneously, intramuscularly, or orally. Compositions can be administered for prophylactic treatment of individuals suffering from, or at risk of a disease or a disorder, e.g., a female experiencing insufficient or inadequate lactation. For therapeutic applications, a pharmaceutical composition is typically administered to a subject suffering from a disease or disorder, e.g., a lactational deficiency, in an amount sufficient to inhibit, prevent, or ameliorate the disease or disorder. An amount adequate to accomplish this is defined as a "therapeutically effective dose."

Although not wishing to be bound by any theory, it is believed that peripherally selective kappa opioid receptor agonist administered to subjects stimulates release of the anterior pituitary hormone prolactin. The compound is typically administered in an amount sufficient to stimulate secretion of prolactin, or stabilize or prevent or inhibit reductions or decreases in prolactin, without causing a severe side effect, such as CNS side effects or diuresis. A useful dose range of a peripherally selective kappa opioid receptor agonist can be determined by one of skill in the art through routine testing. One skilled in the art recognizes that a dose depends, in part, upon physical characteristics of the patient to be treated, e.g., body weight, as well as the route of administration, e.g., intravenous injection or transdermal delivery, and the bioavailability and plasma clearance of the compound by that route of administration, as well as the kappa opioid receptor affinity of the compound. One method of approximating an effective dose is to titrate the dose to achieve a plasma concentration of drug that exceeds the affinity constant (Kd or Ki) of the drug for the kappa opioid receptor, e.g., as determined by a conventional radioreceptor assay as is routinely employed in the art. One method is to titrate the dose to effect, e.g., to employ a dose that is found to effectively elevate prolactin levels, as measured by an immunoassay selective for prolactin. In this case, although only two samples of blood, before and after drug administration, are necessary to compare the basal prolactin level with the stimulated prolactin level, it is typical to measure the stimulated hormonal levels at timed intervals so that the dosing interval can be adjusted to maintain a persistently elevated prolactin level. Serum prolactin concentrations can be assessed by any of several validated methods as are known in the art, e.g., a prolactin-specific immunoassay, e.g., the IMx prolactin assay (Abbott Laboratories, Abbott Park, Ill.), a microparticle enzyme immunoassay used in conjunction with an Abbott IMx Automated Immunoassay Analyzer. When the desired therapeutic effect is to increase lactation, an additional method of dose titration is to employ a prolactin-elevating dose that effectively increases the amount of milk that can be expressed, for example, to between about 500 to 1000 ml per day for a nursing human mother, with the level of milk expression selected according to the needs of the nursing infant. The needs of the nursing infant can be assessed by methods known to those with skill in the art, and which can include evidence for adequate lactation: (1) infant is satisfied after breast feeding, (2) infant gains weight appropriately in relation to age/length, (3) breast engorgement and/or leaking occurs if infant feeding is missed, and (4) milk is secreted in volumes above 500 ml/day. The volume of milk ingested by infants is commonly estimated as 150 ml/kg/day.

The American Academy of Pediatrics has placed an emphasis on increasing breastfeeding in the United States, and has noted that most drugs likely to be prescribed to the nursing mother should have no effect on milk supply or on infant well being (American Academy of Pediatrics, Committee on Drugs. The Transfer of Drugs and Other Chemicals Into Human Milk. *Pediatrics* 108:776-789, 2001). Methods of the invention therefore include those that minimize transfer of a compound or compounds of the invention into breast milk that is fed to an offspring, such as an infant. The transfer of drugs into breast milk is most commonly described quantitatively using the milk to plasma (M/P) concentration ratio. The accuracy of this value is improved if it is based on the area under the concentration time curves (AUC) of the drug in maternal milk and plasma.

The infant daily dose can be estimated with the following equation:

$$\text{Estimated Daily Infant Dosage (mg/kg/day)} = M/P \times \text{average maternal serum concentration} \times 150 \text{ mL/kg/day}$$

In this case M/P (milk to plasma ratio) is the ratio of $AUC_{milk}$ to $AUC_{plasma}$. The average maternal serum concentration refers to AUC after maternal ingestion of a single dose of drug or at steady state during chronic maternal dosing (Bennett 1988, 1996). When using this approach to estimate daily infant dosage, the AUC is either the AUC from time zero to infinity after maternal ingestion of a single dose of drug or the AUC within a dosing interval at steady state during chronic maternal dosing. The volume of milk ingested by infants is commonly estimated as 150 ml/kg/day. The infant dose (mg/kg) can then be expressed as a percentage of the maternal dose (mg/kg). Compounds of the invention can result in an infant dose of less than 10% of the maternal dose, or less than 1% or less than 0.1% of the maternal dose. Since compounds of the invention include peptides, they can be formulated, e.g., with polymeric microspheres, to protect them from degradation and enhance absorption in the gastrointestinal tract (e.g., Mahato R I. Emerging trends in oral delivery of peptide and protein drugs. *Crit. Rev. Ther. Drug Carrier Syst.* 20:153 214, 2003). Microsphere-encapsulated peptides, for example typically do not survive the maternal gastrointestinal environment and release free peptide into the circulation, such that peptides would be orally bioavailable to the offspring through breast milk in significant amounts, which can be readily confirmed by drug assay of infant plasma and/or urine.

The utility of the present invention is not limited to promoting, elevating, increasing or stabilizing lactation in human and non human mammals. Although the prolactin receptor is indeed found in the mammary gland and the ovary, two of the best characterized sites of prolactin actions in mammals, the receptor is also found in areas of the brain that are outside the blood brain barrier, and are therefore accessible to circulating prolactin (Freeman M E et al. Prolactin: Structure, function, and regulation of secretion. *Physiol. Rev.* 80:1523-1631, 2000). In particular, the prolactin receptor (and/or the mRNA encoding the prolactin receptor) is found in the choroid plexus the area postrema, and the mediobasal hypothalamus. Prolactin receptors are also present in a wide range of peripheral tissues, including the pituitary gland, heart, lung, thymus, spleen, liver, pancreas, kidney, adrenal gland, uterus, skeletal muscle, and skin. Accordingly, it is contemplated that peripherally selective kappa opioid receptor agonists, as described herein, will be useful in preventing, ameliorating or modulating conditions associated with these regions of the brain and periphery, as well. Thus, for example, elevated circulating prolactin, caused by a compound of the instant invention, would have access to the mediobasal hypothalamus, a region outside the blood-brain barrier that includes the anterior periventricular area, paraventricular nucleus, and arcuate nucleus (e.g., Merchenthaler I. Neurons with access to the general circulation in the central nervous system of the rat: a retrograde tracing study with fluoro gold. *Neuroscience* 44:655-62, 1991). These hypothalamic nuclei are critical for neuroendocrine regulation, and contain prolactin receptors, which would thereby be therapeutically affected, e.g., in neuroendocrine related disorders, by elevations in circulating prolactin caused by a compound of the instant invention.

A variety of assays may be employed to test whether the compounds of the invention exhibit high affinity and selectivity for the kappa opioid receptor, long duration of in vivo bioactivity, lack of CNS side effects, and prolactin elevating activity. Receptor assays are known in the art and kappa opioid receptors from several species have been cloned, as have mu and delta opioid receptors. Kappa opioid receptors as well as mu and delta opioid receptors are classical, seven transmembrane spanning, G-protein coupled receptors. Although these cloned receptors readily allow a particular candidate compound, e.g., a peptide, to be screened, natural sources of mammalian opioid receptors are also useful for screening, as is well known in the art (Dooley C T et al. Selective ligands for the mu, delta, and kappa opioid receptors identified from a single mixture based tetrapeptide positional scanning combinatorial library. *J. Biol. Chem.* 273: 18848-56, 1998). Thus, screening against both kappa and mu opioid receptors, whether of recombinant or natural origin, may be carried out in order to determine the selectivity of the compound(s) for the kappa over the mu opioid receptor. In general, a mammalian form of the opioid receptor is used for screening; typically, the species source of the receptors is the same as the species for which the compound of the invention is being assessed, e.g., human placental tissue as a source of kappa opioid receptors (Porthe G et al. Kappa opiate binding sites in human placenta. *Biochem. Biophys. Res. Commun.* 101:1-6, 1981) for screening if the contemplated use of the screened compounds is for treatment of a human subject.

Binding affinity refers to the strength of interaction between ligand and receptor. To demonstrate binding affinity for opioid receptors, the compounds of the invention can be evaluated using competition binding studies. These studies can be performed using cloned kappa and mu opioid receptors expressed in stable transfected cell lines or naturally occurring opioid receptors from a receptor-enriched tissue source, as noted above. In these studies, the test compounds (unlabeled or cold ligand) are used at increasing concentrations to displace the specific binding of a radiolabeled ligand that has high affinity and selectivity for the receptor studied. Tritiated U-69,593 and DAMGO can be used as ligands in kappa and mu opioid receptor studies, respectively. Both ligands are commercially available (NEN-Dupont). DAMGO is an acronym for [D-Ala$^2$, MePhe$^4$, Gly-ol$^5$]-enkephalin. The affinity of the radioligands is defined by the concentration of radioligand that results in half-maximal specific binding ($K_D$) in saturation studies. The affinity of the test compound (unlabeled or cold ligand) is determined in competition binding studies by calculating the inhibitory constant ($K_i$) according to the following formula:

$$K_i = IC_{50}/[1+(F/K_D)]$$

where $IC_{50}$=Concentration of the cold ligand that inhibits 50% of the specific binding of the radioligand
F=free radioligand concentration
$K_D$=affinity of the radioligand determined in saturation studies.

When performing these assays under specific conditions with relatively low concentrations of receptor, the calculated $K_i$ for the test compound is a good approximation of its dissociation constant $K_D$, which represents the concentration of ligand necessary to occupy one-half (50%) of the binding sites. A low $K_i$ value in the nanomolar and subnanomolar range is considered to identify a high affinity ligand in the opioid field. Exemplary analogs have a $K_i$ for kappa opioid receptor of about 10 nanomolar (nM) or less, and typical analogs have a $K_i$ of about 1 nM or less. High affinity compounds: (1) enable the use of relatively low doses of drug, which minimizes the likelihood of side effects due to low affinity interactions, and (2) potentially reduce the cost of manufacturing a dose since a correspondingly smaller amount of a higher affinity compound would be required to produce the desired therapeutic effect, assuming equal absorption, distribution, metabolism, and excretion.

These binding assays employing kappa opioid receptors and mu opioid receptors are straightforward to perform and can be readily carried out with large numbers of compounds to determine whether such compounds are kappa opioid receptor selective and have high affinity. Such binding assays can be carried out in a variety of ways as well known to one of skill in the art, and one detailed example of an assay of this general type is set forth in Young E A et al. [$^3$H]Dynorphin A binding and kappa selectivity of prodynorphin peptides in rat, guinea pig and monkey brain. *Eur. J. Pharmacol.* 121:355-65, 1986.

Various abbreviations used herein are as follows:
By D-Nle is meant D-norleucine, and D-Hle represents D-homoleucine. D-Har represents D-homoarginine, and D-nArg represents D-norarginine which is one carbon shorter than D-Arg. By D-Nal is meant the D-isomer of alanine which is substituted by naphthyl on the β-carbon.

Typically, D-2Nal is employed, i.e. the attachment to naphthalene is at the 2-position on the ring structure; however, D-1Nal may also be used. The abbreviations D-Cpa and D-Fpa are used to represent, respectively, chloro-D-Phe and fluoro-D-Phe, with D-4Cpa, D-2Fpa, D-3Fpa and D-4Fpa being typical. D-Npa means nitro-D-Phe, and D-Mpa is used to represent methyl D-Phe. D-3,4Cpa means 3,4-dichloro-D-Phe. D-Acp represents D-Ala(cyclopentyl). D-Orn represents D-ornithine, and D-Dbu represents alpha, gamma-diamino butyric acid. CML represents $C^{alpha}$methyl Leu, and CMP and CMO represent $C^{alpha}$ Me Phe and $C^{alpha}$ Me Orn. By D-4Amf is meant D-4(NH$_2$CH$_2$)Phe, and by D-Gmf is meant Amf(amidino) which represents D-Phe where the 4-position is substituted with CH$_2$NHC(NH)NH$_2$. Amd represents amidino, and the symbol D-Amf(Amd) is also used. By D-Tic is meant D-1,2,3,4-tetrahydroisoquinoline-3-carboxylic acid. In Ala(Thi), Thi represents the thienyl group, which is typically linked at its 2-position to alanine, although 3-thienyl is an equivalent. By Ily and Ior are respectively meant isopropyl Lys and isopropyl Orn where the side chain amino group is alkylated with isopropyl.

By lower alkyl is meant $C_1$ to $C_6$, for example, $C_1$-$C_4$ but including cyclopropyl and cyclobutyl. Me, Et, Pr, Ipr, Bu, Pn and Bzl are used to represent methyl, ethyl, propyl, isopropyl, butyl, pentyl and benzyl. By Cyp is meant cyclopropyl, and by Cyb is meant cyclobutyl. Although the linkage is typically to one end of an alkyl chain, the linkage may be elsewhere in the chain, e.g. 3-pentyl which may also be referred to as ethylpropyl. 4Nbz and 4Abz represent 4-nitrobenzyl and 4-aminobenzyl. By 2-, 3- and 4-picolyl (Pic) are meant methylpyridine groups with the attachment being via a methylene in the 2-, 3- or 4-position.

By Mor is meant morpholinyl,

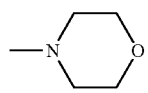

and by Tmo is meant thiomorpholinyl,

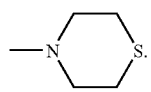

Ahx is used to represent 4-aminocyclohexyl, and hEt is used to represent hydroxyethyl, i.e.—CH$_2$ CH$_2$ OH. Aeb is used to represent 4-(2-amino-2-carboxyethyl)benzyl, i.e.

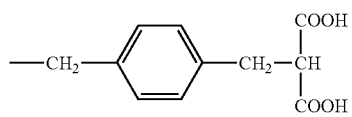

By Pip is meant piperidinyl, and by 4-HyP and OxP are meant 4-hydroxypiperidinyl and 4-oxo-piperidinyl. By Ppz is meant piperazinyl. Ecp represents 4-ethylcarbamoylpiperazinyl; quaternary ammonium moieties, such as 4-dimethyl piperazinyl (Dmp) or other di-lower alkyl substitutions, may also be used. Substituted benzyl is typically 4-aminobenzyl, i.e.

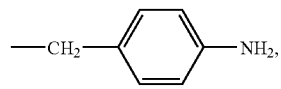

and by 2-Tzl is meant 2-thiazolyl, i.e.

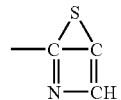

By Dor is meant δ-ornithinyl where the side chain amino group of L-ornithine is connected by an amide bond to the C-terminus.

D-Phe or substituted D-Phe is an example at the 1-position. The phenyl ring may be substituted at the 2-, 3- and/or 4-positions, and commonly substitutions by chlorine or fluorine at the 2 or 4-position are particular examples. The alpha-carbon atom may also be methylated. Other equivalent residues which resemble D-Phe may also be used, and these include D-Ala(cyclopentyl), D-Ala(thienyl), D-Tyr and D-Tic. The 2-position residue can also be D-Phe or substituted, D-Phe with such substitutions including a substituent on the 4-position carbon of the phenyl ring or the 3- and 4-positions. Alternatively, D-alanine substituted by naphthyl can be used, as well as D-Trp and D-Tyr. The 3-position can be occupied by a residue such as D-Nle, D-Leu, D-CML, D-Hle, D-Met or D-Val; however, D-Ala(cyclopentyl) or D-Phe may also be used. D-Arg and D-Har, which may be substituted with diethyl, are examples for the 4-position; however, D-nArg and other equivalent residues may be used, such as D-Lys or D-Orn (either of which can have its omega-amino group alkylated as by isopropyl or have its α-carbon group methylated). Moreover, D-Dbu, D-4Amf (which is typically substituted with amidino), and D-His may also be used.

CHART OF ADDITIONAL FORMULA ABBREVIATIONS

| Abbreviation | Definition |
|---|---|
| D-Phe | D-phenylalanine |
| D-Tyr | D-tyrosine |
| D-Tic | D-1,2,3,4-tetrahydroisoquinoline-3carboxylic acid |
| D-Ala | D-alanine |
| D-1Nal | D-Alanine substituted by naphthyl on the beta carbon with the point of attachment at the 1-position on the naphthyl ring structure |
| D-2Nal | D-Alanine substituted by naphthyl on the beta carbon with the point of attachment at the 2-position on the naphthyl ring structure |
| D-Trp | D-tryptophan |
| D-Nle | D-norleucine |
| D-Leu | D-leucine |
| D-Hle | D-homoleucine |
| D-Met | D-methionine |
| D-Val | D-valine |
| D-Arg | D-arginine |
| D-Har | D-homoarginine |
| D-nArg | D-norarginine |
| D-Lys | D-lysine |
| D-Ily | Isopropyl-D-lysine |
| D-Arg(Et$_2$) | diethyl-D-arginine |
| D-Har(Et$_2$) | diethyl-D-homoarginine |
| D-Amf | D-(NH$_2$CH$_2$)-Phenylalanine |

-continued

| Abbreviation | Definition |
|---|---|
| D-Gmf | D-($CH_2NHC(NH)NH_2$)-Phenylalanine |
| D-Dbu | Alpha, gamma-diamino butyric acid |
| D-Orn | D-ornithine |
| D-Ior | Isopropyl-D-ornithine |
| Aeb | 4-(2-amino-2-carboxyethyl)benzyl |
| Ppz | piperazinyl |
| Pcp | 4-phenyl carbamoyl piperazin-1-yl |
| Aao | 8-(acetylamino)-3,6-dioxaoct-1-yl |
| Aoo | 8-amino-3,6-dioxaoct-1-yl |
| Hoh | 6-(L-hydroorotylamino)-hex-1-yl; L-hydroorotic acid is $C_4N_2H_5(O)_2$—COOH |
| Ghx | 6-(D-gluconylamino)-hexyl |
| Gao | 6-(D-gluconylamino)-3,6-dioxaoct-1-yl |
| D-4Fpa | 4-fluoro-D-phenylalanine |
| D-4Cpa | 4-chloro-D-phenylalanine |
| D-3,4Cpa | 3,4-dichloro-D-phenylalanine |
| D-CML | $C^\alpha$methyl-D-Leucine |
| D-Acp | D-Ala(cyclopentyl) |
| Mor | Morpholinyl |
| Tmo | thiomorpholinyl |
| Pip | Piperidinyl |
| 4-HyP | 4-hydroxy piperidin-1-yl |
| OxP | 4-oxo-piperidin-1-yl |
| Me | Methyl |
| Et | Ethyl |
| Pr | Propyl |
| Bu | Butyl |
| HEt | Hydroxyethyl (i.e., —$CH_2CH_2OH$) |
| Cyp | Cyclopropyl |
| Bzl | Benzyl |
| D-2Fpa | 2-fluoro-D-phenylalanine |
| D-Ala(2Thi) | 2-thienyl-D-alanine |
| 4Pic | 4-picolyl |
| $C^\alpha$methyl | Methyl attached to the alpha carbon of an amino acid |

In one embodiment, the invention provides a method of treating a mammal exhibiting insufficient or inadequate milk production or at risk of insufficient or inadequate milk production; wherein the method includes administering to the mammal an amount of a peripherally selective kappa opioid receptor agonist or salt thereof or prodrug thereof effective to treat the mammal, the peripherally selective kappa opioid receptor agonist or salt thereof or prodrug thereof being a peptide, or ionizes or is metabolized to form a peptide having the formula:

H—$Xaa_1$-$Xaa_2$-$Xaa_3$-$Xaa_4$-Q; and wherein $Xaa_1$ is (A)D-Phe, ($C^{alpha}$ Me)D-Phe, D-Tyr, D-Tic or D-Ala(cyclopentyl or thienyl), with A being H, $NO_2$, F, $C_1$ or $CH_3$; $Xaa_2$ is (A')D-Phe, D-1Nal, D-2Nal, D-Tyr or D-Trp, with A' being A or $3,4Cl_2$; $Xaa_3$ is D-Nle, (B)D-Leu, D-Hle, D-Met, D-Val, D-Phe or D-Ala(cyclopentyl) with B being H or $C^{alpha}$ Me; $Xaa_4$ is D-Arg, D-Har, D-nArg, D-Lys, D-Lys (Ipr), D-Arg($Et_2$), D-Har($Et_2$), D-Amf(G), D-Dbu, (B)D-Orn or D-Orn(Ipr), with G being H or amidino; and Q is $NR_1$, $R_2$, morpholinyl, thiomorpholinyl, (C)piperidinyl, piperazinyl, 4-mono- or 4,4-di-substituted piperazinyl or delta-ornithinyl, with $R_1$ being lower alkyl, substituted lower alkyl, benzyl, substituted benzyl, aminocyclohexyl, 2-thiazolyl, 2-picolyl, 3-picolyl or 4-picolyl, $R_2$ being H or lower alkyl; and C being H, 4-hydroxy or 4-oxo. In a particular embodiment $Xaa_2$ is D-Phe, $Xaa_3$ is D-Nle and $Xaa_4$ is D-Arg. In another embodiment Q is $NHR_1$ and $R_1$ is ethyl, propyl, butyl, cyclopropyl or cyclobutyl. In an alternative embodiment, Q is morpholinyl or thiomorpholinyl; or Q is $NHR_1$ and $R_1$ is 4-picolyl. In another embodiment, $Xaa_1$ is D-Ala(2-thienyl); alternatively, $Xaa_1$ is D-4FPhe and $Xaa_2$ is D-4ClPhe. In still another embodiment, $Xaa_3$ is D-Nle or D-Leu and $Xaa_4$ is D-Orn or D-Amf(Amd). In another embodiment, $Xaa_2$ is D-Phe, $Xaa_3$ is D-Leu or D-CML and $Xaa_4$ is D-Orn.

The invention further provides a method of treating a mammal exhibiting insufficient or inadequate milk production or at risk of insufficient or inadequate milk production; wherein the method includes administering to the mammal an amount of a peripherally selective kappa opioid receptor agonist or salt thereof or prodrug thereof effective to treat the mammal, the peripherally selective kappa opioid receptor agonist or salt thereof or prodrug thereof being a peptide, or ionizes or is metabolized to form a peptide having the formula:

H—$Xaa_1$-$Xaa_2$-$Xaa_3$-$Xaa_4$-Q; and wherein $Xaa_1$ is D-Phe (unsubstituted or substituted by $C^{alpha}$, Me, 2F, 4F or 4Cl) or D-Ala(cyclopentyl or thienyl); $Xaa_2$ is (A')D-Phe, D-1Nal, D-2Nal or D-Trp, with A' being H, 4F, 4Cl, $4NO_2$ or $3,4Cl_2$; $Xaa_3$ is D-Nle, D-Leu, D-CML, D-Met or D-Acp; $Xaa_4$ is D-Arg, D-Arg($Et_2$), D-Lys, D-Ily, D-Har, D-Har($Et_2$), D-nArg, D-Orn, D-Ior, D-Dbu, D-Amf, and D-Amf(Amd); and Q is $NR_1R_2$, Mor, Tmo, Pip, 4-Hyp, OxP or Ppz, with $R_1$ being Me, Et, Pr, Bu, hEt, Cyp, Bzl or 4-picolyl, and $R_2$ being H or Et. In one embodiment, $Xaa_2$ is D-Phe, $Xaa_3$ is D-Nle and $Xaa_4$ is D-Arg. In another embodiment, Q is $NHR_1$, and $R_1$ is ethyl, propyl, butyl, cyclopropyl or cyclobutyl. Alternatively, Q can be morpholinyl or thiomorpholinyl. In a further embodiment, Q is $NHR_1$, and $R_1$ is 4-picolyl. Alternatively, Q is $NR_1R_2$ and $R_1$ is ethyl and $R_2$ is ethyl. In yet another embodiment, $Xaa_1$ is D-Phe or D-Ala(2-thienyl) and $Xaa_2$ is D-4ClPhe. In another embodiment, $Xaa_3$ is D-Nle or D-Leu and Q is morpholinyl.

In a particular embodiment, $Xaa_1$ is D-Phe, D-4Fpa, D-2Fpa, D-Acp or D-Ala(2Thi); $Xaa_2$ is (A)D-Phe, D-1Nal, D-2Nal or D-Trp, with A being 4F or 4Cl; $Xaa_3$ is D-Nle, D-Met or D-Leu; $Xaa_4$ is D-Arg, D-Har, D-nArg, D-Lys, D-Orn or D-Amf(Amd); and Q is $NHR_1$, Mor, Tmo, Pip or Ppz, with $R_1$ being Et, Pr or 4Pic.

In another particular embodiment, the peptide has the formula:

H-D-Phe-D-Phe-D-Nle-D-Arg-NHEt,

H-D-Phe-D-Phe-D-Nle-D-Arg-morpholinyl,

H-D-Phe-D-Phe-D-Nle-D-Arg-NH-4-picolyl,

H-D-Phe-D-Phe-D-Nle-D-Arg-NHPr,

H-D-Phe-D-Phe-D-Nle-D-Arg-thiomorpholinyl,

H-D-Phe-D-Phe-D-Nle-D-Arg-$Net_2$,

H-D-Phe-D-Phe-D-Nle-D-Arg-NHMe,

H-D-Phe-D-Phe-D-Leu-D-Orn-morpholinyl,

H-D-Phe-D-Phe-D-Nle-D-Arg-NHhEt,

H-D-Phe-D-Phe-D-Nle-D-Arg-NH-cyclopropyl,

H-D-Ala(2Thi)-D-4 Cpa-D-Leu-D-Arg-morpholinyl,

H-D-Phe-D-Phe-D-Nle-D-Arg-piperidinyl,

H-D-Phe-D-Phe-D-Leu-D-Orn-NHEt,

H-D-Phe-D-Phe-D-Leu-D-Lys-morpholinyl, or

H-D-Phe-D-Phe-D-Nle-D-Arg-piperazinyl.

Mammals exhibiting insufficient or inadequate milk production or at risk of insufficient or inadequate milk production can be treated by a method according to the present invention; the method includes administering to the mammal an amount of a peripherally selective kappa opioid receptor agonist or salt thereof or prodrug thereof effective to treat the mammal, wherein the administration includes intravenous, subcutaneous, intramuscular, intranasal, oral, or transdermal administration, such as for instance by an electrotransport device. In one embodiment of the method the electrotransport device delivers the peripherally selective kappa opioid receptor agonist through a body surface.

In one particular aspect, the method includes: (a) providing a first electrode; (b) providing a second electrode; (c) providing a power source electrically connected to said first and said second electrodes; (d) providing at least one donor reservoir having the peripherally selective kappa opioid receptor agonist, wherein said donor reservoir is associated with said first or second electrode; and (e) delivering a therapeutically effective amount of said peripherally selective kappa opioid receptor agonist through said body surface.

The peripherally selective kappa opioid receptor agonist can administered by any of these methods between about 1 microgram/kg of body weight to about 100 milligrams/kg of body weight of said mammal per hour, day, week or month. These methods of the invention delivering the peripherally selective kappa opioid receptor agonist administered can increase prolactin to levels greater than 10, 15, 20, 25, 50, 75, 100, 125, 150, 175, or 200 ng/ml serum above the baseline level of serum prolactin. These methods are particularly advantageous for the treatment of female animal subjects (particularly a mammal, such as for instance a primate, ungulate, canine or feline) or human patients, especially pregnant females or females that have given birth to an offspring within 1, 2, 3, 4, 5, 6, 7, 8, 9, 10, 1, 12, 12-24, 24-26, 36-48 hours, days, weeks, or months. Suitable primates include an ape, gorilla, monkey, macaque, chimpanzee, lemur or orangutan. Suitable ungulates include a cow, pig, sheep, goat or horse.

The invention further provides a method of treating a mammal exhibiting an insufficient or inadequate amount of milk production or at risk of exhibiting an insufficient or inadequate amount of milk production, wherein the method includes administering to the subject prior to or after childbirth an amount of a peripherally selective kappa opioid receptor agonist in conjunction with a lactation enhancer, such as for instance, oxytocin or a stabilizer effective to treat the mammal. The oxytocin can be administered within one or more hours, days, or weeks following childbirth. In a particular embodiment, the lactation enhancer or stabilizer is administered within one or more hours, days, or weeks following childbirth.

This invention is further illustrated by the following examples which in no way should be construed as being further limiting. The contents of all cited references (including literature references, issued patents, published patent applications, and co pending patent applications) cited throughout this application are hereby expressly incorporated by reference.

EXAMPLES

The safety, tolerability, pharmacokinetics, and prolactin-elevating activity of ascending single intravenous (IV) doses of one of the compounds of the instant invention, D-phenylalanyl-D-phenylalanyl-D-norleucyl-N-(4-pyridinylmethyl)-D-argininamide, acetate salt, herein designated as CR665, was assessed in healthy male and surgically sterile female human subjects following 1-hour or 5-minute infusions. CR665, also referenced in the literature as FE 200665, is a peripherally selective kappa opioid receptor agonist; see U.S. Pat. No. 5,965,701; also Riviere P. J.-M. et al. Novel D-amino acid tetrapeptides demonstrate unprecedented k-opioid receptor selectivity and antinociception. 30th Int. Narcotics Res. Conf. (INRC) 1999, Saratoga Springs, N.Y., Jul. 10-12, 1999; Wisniewski K et al. Long acting, selective, peripheral kappa agonists. 26th European Peptide Symposium, Montpilier, France, September 11-15, 2000; Binder W et al. Analgesic and antiinflammatory effects of two novel kappa-opioid peptides. *Anesthesiology*. 94: 1034-44, 2001; Riviere P J. Peripheral kappa-opioid receptor agonists for visceral pain. *Br J. Pharmacol.* 141:1331-4, 2004).

Study Design and Procedures

This clinical study was conducted as a double blind, placebo controlled, ascending single intravenous (IV) dose, sequential group study. The results reported herein were obtained with 54 male and female human subjects in fifteen groups as shown in Table X below. This study was double blind and placebo controlled in order to avoid bias in the collection and evaluation of data during its conduct. Placebo was chosen as the control treatment to assess whether any observed effects were treatment related or simply reflected the study conditions. In each group, subjects received CR665 or placebo. Doses were administered as a single constant rate IV infusion over 1 hour (part A) or 5 minutes (part B) on the morning of Day 1. Doses were administered in an escalating manner following satisfactory review of the safety data and pharmacokinetic data from the lower dose levels. There was a minimum of 6 days between dose escalations to allow sufficient time for an adequate safety review.

Dose levels were as shown in Table 1:

TABLE 1

Treatments

| Part | Group | Population | Treatment | Infusion duration |
|------|-------|------------|-----------|-------------------|
| A | A1 | Males | 0.015 mg/kg/placebo | 1 hour |
|   | A2 | Males | 0.03 mg/kg/placebo | 1 hour |
|   | A3 | Males | 0.06 mg/kg/placebo | 1 hour |
|   | A4 | Males | 0.12 mg/kg/placebo | 1 hour |
|   | A5 | Males | 0.24 mg/kg/placebo | 1 hour |
|   | A6 | Males | 0.48 mg/kg/placebo | 1 hour |
|   | A7 | Males | 0.36 mg/kg/placebo | 1 hour |
|   | A8 | Males | 0.48 mg/kg/placebo | 1 hour |
|   | A9 | Females | 0.24 mg/kg/placebo | 1 hour |
|   | A10 | Females | 0.42 mg/kg/placebo | 1 hour |
|   | A12 | Males | 0.42 mg/kg/placebo | 1 hour |
| B | B1 | Males | 0.03 mg/kg/placebo | 5 minutes |
|   | B2 | Females | 0.06 mg/kg/placebo | 5 minutes |
|   | B3 | Males | 0.06 mg/kg/placebo | 5 minutes |
|   | B4 | Males | 0.09 mg/kg/placebo | 5 minutes |

CR665 was prepared according to Good Manufacturing Practice (GMP) standards and provided as bulk supply in 2 mL glass vials, each containing CR665 solution (1.1 mL at a concentration of 10 mg/mL [free base] in isotonic 0.04 M acetate buffer, pH 4.5). Placebo solution (isotonic 0.04 M acetate buffer, pH 4.5) for IV administration, of identical appearance, i.e., a clear, colorless, solution, was also prepared. The IV dose solutions were stored at 2° C. to 8° C.

The individual intravenous dose for each subject was prepared from bulk supplies (2 mL vials containing 1.1 mL of CR665 or placebo solution). For each dose preparation, an appropriate volume of CR665 solution (10 mg/mL) or placebo solution was withdrawn from one or more vials using a syringe, and injected into a 60 mL Plastipak polypropylene syringe (Beckton Dickinson S.A., Spain) containing an appropriate volume of sterile NaCl buffer.

For the 1 hour infusions the final volume prepared was 40 mL, of which 30 mL was infused. The dose calculation was as follows:

$$\text{Volume of } CR665 \text{ required (mL)} = \text{Dose level} \times \text{body weight} \times \left(\frac{\left[\frac{40}{30}\right]}{10}\right)$$

$$\text{(mg/kg)} \quad \text{(kg)}$$

Volume of buffer = 40 mL volume of CR665 required (mL)

Table 2 provides some example dilutions, based on a 70 kg body weight.

TABLE 2

| Dose level (mg/kg) | CR665 dose to be infused for a 70 kg person (mg/30 mL) | CR665 dose to be prepared (mg/40 mL) | Concentration of dose solution (mg/mL) | CR665 solution[a] volume (mL) | NaCl buffer volume (mL) |
|---|---|---|---|---|---|
| 0.015 | 1.05 | 1.40 | 0.04 | 0.14 | 39.86 |
| 0.03 | 2.10 | 2.80 | 0.07 | 0.28 | 39.72 |
| 0.06 | 4.20 | 5.60 | 0.14 | 0.56 | 39.44 |
| 0.12 | 8.40 | 11.20 | 0.28 | 1.12 | 38.88 |
| 0.24 | 16.80 | 22.40 | 0.56 | 2.24 | 37.76 |

[a]Concentration 10 mg/mL

The dose was administered via a cannula inserted into a suitable vein of the forearm in the non dominant arm of the subject. The dose was infused over a 1 hour period in the morning between 07:00 and 10:30, using an IMED Gemini PC 1 infusion pump operating at a constant rate of 0.5 mL/min (30 mL/h). A total of 30 mL of dosing solution (from 40 mL in the syringe) was administered, and the subjects remained supine throughout the infusion.

From 24 hours after the start of the infusion, meals were provided at appropriate times on each day. Other than the fluid restrictions on Day 1, water was freely available at all times. The volume of fluid consumed up to 24 hours after the start of the infusion was recorded as part of the fluid balance assessment. Subjects fasted from food and beverages (other than water) from 22:00 on Day 1, until the clinical laboratory samples had been taken on the following day, and for at least, 6 hours prior to the follow up visit.

On arrival at the clinical study center on Day −1, pre dose assessments were performed, including testing a urine sample for the presence of illicit drugs, administering an alcohol breath test, and the recording of body weight (in underclothes). Subjects then commenced a 24 hour urine collection for assessment of creatinine clearance and fluid balance. Vitals signs and 12 lead ECG were also assessed, and all subjects received a physical examination.

The condition of each subject was monitored throughout the study. In addition, any signs or symptoms were observed and elicited by open questioning, such as "How have you been feeling since you were last asked?" at the following times for each part of the study: Pre dose, 0.5, 1, 3, 12, 24, 36 and 48 hours after the start of the infusion (up to 24 hours only for Groups A1 to A4), and at Follow up assessment.

Subjects were also encouraged to spontaneously report adverse events occurring at any other time during the study. Any adverse events and remedial action required were to be recorded for each subject. The nature, time of onset, duration and severity were documented, together with the Project Physician's opinion of the relationship to drug administration.

The condition of the dosing cannula site for each subject was monitored for erythema, pruritus and swelling at the following times: Pre dose, 0.5, 1, 2 and 24 hours after the start of the infusion. Subjects were also encouraged to spontaneously report adverse events relating to the infusion site at any other time during the study. Any adverse events and observations relating to the infusion site and remedial action required were to be recorded for each subject. The nature, time of onset, duration, and severity were to be documented, together with the Project Physician's opinion of the relationship to drug administration.

Supine and standing blood pressure, supine pulse rate and oral body temperature were measured in duplicate at the following times: Day 1; Pre dose, 15 minutes (Part B only), 30 minutes, 55 minutes, 1.5, 2, 2.5, 3, 4, 8, 12, 24 and 48 hours after the start of the infusion (up to 24 hours only for Groups A1 to A4); and at Follow up visit. Supine vital signs only were measured during the infusion period. Pre dose blood pressure and pulse rate were measured in triplicate at approximately 2 minute intervals. The median value was used as the baseline value in the data analysis. All subsequent measurements were performed singly, but repeated in duplicate if outside the relevant clinical reference ranges. If repeated, the median of the three values were used in the data analysis. Blood pressure and pulse rate were measured using automated Critikon Dinamap™ PRO 400 monitors. Subjects were required to be supine for at least 5 minutes before blood pressure and pulse rate measurements. Standing blood pressure and pulse rate were then measured singly after the subject had been sitting for approximately 1 minute and then standing for approximately 2 minutes. Oral body temperature was measured singly using an Omron digital thermometer. To assess drug effects on cardiovascular function, a 12 lead resting ECG with a 10 second rhythm strip was recorded on a Marquette MAC5000 ECG machine at the following times, after the subject has been supine for at least 5 minutes: Day 1; Pre dose, 50 minutes, 2, 4, 8, 24 and 48 hours after the start of the infusion (up to 24 hours only for Groups A1 to A4); and at the follow up visit. The ECG machine computed the PR, QT and QTc intervals, QRS duration, and heart rate. The QT interval was corrected for heart rate (QTc) using Bazett's formula. For continuous ECG measurements, continuous cardiac Holter monitoring of each subject, using Reynolds Tracker II Holter monitors, was performed from 1 hour prior to until 4 hours after the start of the infusion. Blood and urine samples were collected, after at least a 6 hour fast, for clinical laboratory evaluations at the following times during the study: Pre dose and 24 hours after the start of the infusion; and at the follow up visit.

The following evaluations were performed, as shown in Table 3.

TABLE 3

| | Units |
|---|---|
| Serum biochemistry: | |
| Aspartate aminotransferase (AST) | IU/L |
| Alanine aminotransferase (ALT) | IU/L |
| Alkaline phosphatase | IU/L |
| Gamma-glutamyl transferase (GGT) | IU/L |
| Sodium | mmol/L |
| Potassium | mmol/L |
| Chloride | mmol/L |
| Calcium | mmol/L |

TABLE 3-continued

|  | Units |
| --- | --- |
| Inorganic phosphate | mmol/L |
| Glucose | mmol/L |
| Urea | mmol/L |
| Bilirubin (total[a]) | μmol/L |
| Creatinine | μmol/L |
| Total protein | g/L |
| Albumin | g/L |
| Urinalysis: | |
| Microscopic examination | + |
| Specific gravity | NA |
| pH | NA |
| Protein | + |
| Glucose | + |
| Ketones | + |
| Blood | + |
| Urobilinogen | + |
| Hematology: | |
| White blood cell count (WBC) | $10^9$/L |
| Red blood cell count (RBC) | $10^{12}$/L |
| Haemoglobin | g/dL |
| Haematocrit (PCV) | % |
| Mean cell volume (MCV) | fL |
| Mean cell haemoglobin (MCH) | pg |
| MCH concentration (MCHC) | g/dL |
| Platelet count | $10^9$/L |
| Differential WBC | $10^9$/L & % |
| Serology: | |
| Hepatitis B surface antigen (HBsAg)[b] | neg/pos |
| Hepatitis C antibody[b] | neg/pos |
| HIV antibodies[b] | neg/pos |

[a]Direct bilirubin analyzed only if total bilirubin is elevated
[b]Analyzed at screening only
Neg = Negative
Pos = Positive Blood samples (2.5 mL) were collected for evaluation of serum prolactin at the following times: Pre dose (in triplicate, with at least a 15 minute interval between each of the triplicate pre dose samples), 15 minutes, 30 minutes, 45 minutes, 1 hour (immediately prior to the end of infusion), 1 hour 5 minutes, 1 hour 10 minutes, 1 hour 15 minutes, 1.5, 2, 2.5, 3, 4, 6, 8 and 12 hours after the start of the infusion (18 samples).

Plasma and urine samples for the analysis of CR665 and N oxide metabolite were prepared by solid phase extraction. The centrifuged eluates were quantified by liquid chromatography with tandem mass spectrometric detection (LC MS/MS). The lower limit of quantification was 1 ng/mL.

After collection of urine samples, following removal of the aliquots for drug assay and/or urinalysis, urine was pooled over the following time intervals: 24 to 0 hours and 0 to 24 hours after the start of the infusion. A 10 mL aliquot was removed from the each pooled collection for determination of urinary creatinine.

An assessment of fluid balance (made by comparison of volume of fluid consumed and volume of fluid excreted) was made over the following periods: 24 to 0 hours and 0 to 24 hours after the start of the infusion. During these periods, the volume of fluid consumed and the volume of urine excreted was recorded.

A full physical examination, including a neurological examination, was performed at the following times: Discharge (Day 2 or 3) and at Follow up visit.

For pharmacokinetic assessments, blood samples (1×3 mL) were taken from the contralateral forearm vein(s) at the following times: Pre-dose, 15 minutes, 30 minutes, 45 minutes, 1 hour (immediately prior to the end of infusion), 1 hour 5 minutes, 1 hour 10 minutes, 1 hour 15 minutes, 1.5, 2, 2.5, 3, 4, 6, 8, 12, 16, 24, 36 and 48 hours after the start of the infusion). An indwelling cannula (Venflon®; BOC Ohmeda AB, Sweden) was used for all blood collection pre-dose and up to at least 12 hours after the start of the infusion. Otherwise, samples were collected using venipuncture. Blood samples were collected into pre-chilled 3 mL $K_3$EDTA Vacutainer™ tubes (Becton Dickinson UK, Ltd., Oxford) and, after mixing, were placed in a cool box containing crushed ice/water. The samples were centrifuged, within 30 minutes of collection, at 1500 g for 10 minutes at approximately 4° C. For each sample, the separated plasma was transferred into two 5 mL suitably labeled polypropylene tubes, and stored immediately at approximately −20° C. Plasma samples were analyzed for CR665 using liquid chromatography with tandem mass spectrometric detection.

Urine was collected into standard weight polyethylene containers over the following time intervals: Pre dose (−24 to 0), 0 to 4, 4 to 8, 8 to 12, 12 to 24 and 24 to 48 hours after the start of the infusion. During each collection period, the containers were stored in a refrigerator at 2 to 8° C. The weight (g) of each collection was recorded prior to removal of two sub samples (each approximately 4 mL) into suitably labeled polypropylene containers, which were stored within 2 hours of collection, at approximately −20° C. Additional aliquots (1×100 mL per collection period) were stored for possible future analyses. Any remaining urine from post dose collection intervals was pooled with the rest of the urine collected during the 0 to 24 hour collection period, for analysis of creatinine clearance. A nominal value for specific gravity of 1.018 was used to calculate urine volume.

The pharmacokinetic analysis was conducted using WinNonlin Enterprise Version 4.0.1.

Pharmacokinetic parameters were determined from the plasma and urine, concentrations of CR665 and the N-oxide metabolite using non compartmental procedures. The pharmacokinetic parameters determined are presented in Table 4 below.

TABLE 4

Pharmacokinetic Parameters Determined for CR665 and the N-Oxide Metabolite

| Parameter | Definition |
| --- | --- |
| $AUC_{0-t}$ | Area under the plasma concentration-time curve from time zero up to the last quantifiable concentration |
| $AUC_{0-\infty}$ | Area under the plasma concentration-time curve from time zero to infinity |
| % $AUC_{ex}$ | Percentage of AUC that is due to extrapolation from $t_z$ to infinity |
| $C_{max}$ | Maximum observed plasma concentration |
| $C_{inf}$ | Plasma concentration at end of the IV infusion |
| $t_{max}$ | Time of maximum observed plasma concentration |
| $t_z$ | Time of last quantifiable plasma concentration |
| $\lambda_z$ | Apparent plasma terminal elimination rate constant |
| $t_{1/2}$ | Apparent plasma terminal elimination half-life |
| $MRT_{int}$ | Intrinsic mean residence time |
| CL | Total plasma clearance (CR665 only) |
| $V_z$ | Apparent volume of distribution during the terminal phase (CR665 only) |
| $V_{ss}$ | Apparent volume of distribution at steady-state (CR665 only) |
| $MR_{AUC}$ | Metabolic ratio based on AUC (N-oxide metabolite only) |
| $MR_{Cmax}$ | Metabolic ratio based on $C_{max}$ (N-oxide metabolite only) |
| Ae | Amount of drug excreted in urine |
| fe | Percentage of dose excreted in urine |
| $CL_R$ | Renal clearance |

Dose and body weight normalized values (norm) were determined for $AUC_{0-t}$, $AUC_{0-\infty}$, $C_{inf}$ and $C_{max}$. Body weight normalized values [norm] were determined for $V_z$, $V_{ss}$, CL and $CL_R$.

The pharmacokinetic analysis was conducted using model independent methods as implemented in WinNonlin software, based on plasma concentrations of CR665 from those subjects who have received CR665 and have evaluable plasma concentration-time profiles.

The following plasma pharmacokinetic parameters were determined for CR665:

$C_{max}$ Maximum plasma concentration $t_{max}$ Time of maximum plasma concentration $t_{1/2z}$ Terminal half-life=$\ln(2)/\lambda_z$ $AUC_{0-t}$ Area under the plasma concentration-time curve from time zero to time t (time of last quantifiable plasma concentration)

$AUC_{inf}$ Area under the plasma concentration-time curve from time zero to infinity calculated as $[AUC_{0-t}+(C_{last}/\lambda_z)]$ where $C_{last}$ is the estimated concentration at the last quantifiable concentration curve.

$\lambda_z$ Terminal-phase rate constant, also known as $K_{el}$

CL Total body clearance=Dose/$AUC_{inf}$ $V_z$ Volume of distribution based on terminal phase calculated as $$Vz/F=Dose/\lambda_z * AUC_{inf}$$

Individual elapsed sampling times were used in the pharmacokinetic analysis. $C_{max}$ and $t_{max}$ were obtained directly from the experimental observations. For the purpose of calculating $AUC_{0-t}$, when two consecutive plasma concentrations below the lower limit of quantification (LLOQ) were encountered after $t_{max}$, all subsequent values were excluded from the analysis. The exponential rate constant of the terminal-phase, $\lambda_z$, was estimated by linear regression of the log concentration-time data associated with the terminal phase of the plasma concentration-time profile. The number of data points included in the regression was determined by visual inspection. A minimum of 3 data points in the terminal phase, excluding $C_{max}$, was required to estimate $\lambda_z$.

An assessment of dose-proportionality of the pharmacokinetics of CR665 was also performed. Log-transformed $AUC_{0-t}$, $AUC_{inf}$ and $C_{max}$ were derived and a model of the form:

$$Log(parameter)=Intercept+\beta*Log(Dose)+Error$$

where dose is a fixed term was fitted to assess a between-subject estimate of the slope in order to assess dose-proportionality. A point estimate of the slope β, with 90% confidence intervals, provides a plausible range for which the true slope occurs. The interpretation of the slope is such that a conclusion of dose-proportionality for $AUC_{0-t}$, $AUC_{inf}$ and $C_{max}$ of CR665 will be made if the 90% CI for the slope contains the value 1.

The pharmacodynamic analysis was conducted using WinNonlin Enterprise Version 4.0.1 (Pharsight Corporation, Mountain View, Calif., USA). The following pharmacodynamic parameters were calculated from the serum concentrations of prolactin:

Change from baseline (mean of triplicate pre-dose values) at each sampling time

Maximum observed change from baseline ($C_{max}$)

Area under the change from baseline time curve from 0 to 12 hours ($AUC_{0-12\,h}$)

This study was conducted under a MHRA Clinical Trials Authorization (CTA) in accordance with: (1) the relevant articles of the Declaration of Helsinki as adopted by the 18th World Medical Assembly in 1964 and as revised in Tokyo (1975), Venice (1983), Hong Kong (1989), South Africa (1996) and Scotland (2000); and (2) the ICH Good Clinical Practices (GCP) consolidated guidelines adopted in the EU by CPMP, July 1996, issued as CPMP/ICH/135/95.

Drug Safety

All 54 subjects completed the treatment period with no severe or serious adverse events. In particular, even at the highest dose levels, there were no signs of the more typical CNS symptoms (hallucinations or dysphoria) associated with intolerable dose levels of previously tested kappa opioid receptor agonists. For the 12-lead ECG evaluations, there were no treatment related trends, significant clinical changes, or abnormalities in the morphology of the 12 lead ECG. Similarly, for the clinical laboratory evaluations, there were no treatment related trends or significant clinical findings in serum biochemistry, hematology, or urinalysis parameters. Physical examination of the subjects also revealed no treatment related findings.

In Parts A and B of the study, there were no treatment or dose related trends in mean supine and standing systolic and diastolic blood pressure, supine and standing pulse rate or oral body temperature. No apparent treatment or dose related trends in the 12 lead ECG-parameters were noted in Parts A and B. In addition, there were no clinically important findings in the morphology of the 12 lead ECGs for individual subjects at each dose level of CR665 There was no evidence of prolongation of QTc interval (Bazett's and Friedericia's corrected) at each dose level of CR665 in male and female subjects.

For Parts A and B, there were no clinically important changes in creatinine clearance, estimated from serum creatinine, for any subject during the study. The mean creatinine clearance was generally similar prior to dosing and at 24 hours after dosing for each dose level of CR665 and placebo. There were no apparent treatment or dose related trends in fluid balance (urine excreted-fluid consumed) over the 0 to 24 hour period after the start of the infusion. However, an increase in the volume of urine excreted over the first 4 hours after the start of the infusion was observed at each dose level of CR655 compared to placebo in male and female subjects for Parts A and B of the study.

Pharmacodynamics: Time Course of Prolactin Elevation by CR665

The administration of single IV doses of CR665 caused a rapid and marked increase in serum concentrations of prolactin across all dose levels in male and female subjects. Changes from baseline (pre dose) in serum concentrations of prolactin following 1-hour and 5-minute infusions of placebo and CR665 in male and female subjects are shown in FIGS. 1 to 3:

The derived pharmacodynamic parameters for serum prolactin following 1-hour and 5-minute infusions of placebo and CR665 in male and female subjects are summarized in Tables 5 to 7:

TABLE 5

Summary of the Pharmacodynamic Parameters of Serum Prolactin
(Changes from Baseline) Following a 1 hour IV Infusion in Male Subjects
(Part A)

| Parameter | Placebo [males] (N = 17) | 0.015 [males] (N = 4) | 0.03 [males] (N = 4) | 0.06 [males] (N = 4) | 0.12 [males] (N = 4) | 0.24 [males] (N = 4) | 0.36 [males] (N = 4) | 0.42 [males] (N = 4) | 0.48 [males] (N = 8) |
|---|---|---|---|---|---|---|---|---|---|
| | | | | | Dose of (mg/kg) | | | | |
| $AUC_{0-12\,h}$ (ng · h/mL) | 0.760 (27.5) | 30.8 (87.6) | 57.4 (30.3) | 43.6 (32.2) | 89.5 (38.6) | 119 (22.3) | 140 (40.0) | 132 (51.5) | 131 (74.5) |
| $C_{max}$ (ng/mL) | 4.61 (3.44) | 22.2 (6.44) | 18.8 (1.47) | 25.3 (6.41) | 39.3 (13.9) | 36.3 (17.3) | 45.5 (16.9) | 44.2 (10.8) | 47.2 (27.4) |

Arithmetic mean (SD) data are presented
N = Number of subjects studied

TABLE 6

Summary of the Pharmacodynamic Parameters of Serum Prolactin
(Changes from Baseline) Following a 1 hour IV Infusion in Female
Subjects (Part A)

| Parameter | Placebo [females] (N = 3) | 0.24 [females] (N = 3) |
|---|---|---|
| | Dose of (mg/kg) | |
| $AUC_{0-12\,h}$ (ng · h/mL) | 19.7 (23.5) | 209 (21.1) |
| $C_{max}$ (ng/mL) | 3.67 (2.27) | 68.2 (14.3) |

Arithmetic mean (SD) data are presented
N = Number of subjects studied

TABLE 7

Summary of the Pharmacodynamic Parameters of Serum
Prolactin (Changes from Baseline) Following a 5 minute IV
Infusion in Male and Female Subjects (Part B)

| Parameter | Placebo [males] (N = 5) | 0.03 [males] (N = 4) | 0.06 [males] (N = 4) | 0.09 [males] (N = 4) | 0.06 [females] (N = 4) |
|---|---|---|---|---|---|
| | | | Dose of (mg/kg) | | |
| $AUC_{0-12\,h}$ (ng · h/mL) | −0.876 (34.1) | 24.3 (35.4) | 74.3 (44.2) | 68.5 (13.5) | 96.8 (32.9) |
| $C_{max}$ (ng/mL) | 4.08 (3.63) | 33.6 (14.3) | 42.0 (22.8) | 37.1 (13.3) | 32.3 (14.8) |

Arithmetic mean (SD) data are presented
N = Number of subjects studied

In Part A, following 1-hour infusions of 0.015 to 0.48 mg/kg CR665 in male subjects, there was a rapid and marked increase in serum prolactin concentrations. At each dose level, maximum serum prolactin concentrations generally occurred at 1 hour after the start of the infusion, i.e. at the end of the infusion. There was an apparent dose-related increase in mean values for $C_{max}$ (maximum changes from baseline in serum prolactin) up to the 0.36 mg/kg dose level. Mean $C_{max}$ values were generally similar at the 0.36, 0.42 and 0.48 mg/kg dose levels, with maximum serum prolactin levels being approximately 5- to 6-fold higher than baseline (pre-dose) across these dose levels. Mean values for $AUC_{0-12\,h}$ (changes from baseline) increased up to 0.36 mg/kg, and thereafter were generally similar over the 0.36 to 0.48 mg/kg dose range. Following maximum concentrations of prolactin, there was a dose-related decrease to baseline levels. Mean values had fallen to close to baseline values by 8 hours at the 0.36, 0.42 and 0.48 mg/kg dose levels.

In Part A, following 1 hour infusions of 0.24 mg/kg CR665 in female subjects, maximum serum prolactin concentrations occurred at 1 hour after the start of the infusion. The mean $C_{max}$ values (change from baseline) in females were higher than in male subjects, with maximum serum prolactin levels being approximately 12-fold greater than baseline (pre dose) in females.

In Part B, following 5-minute infusions of 0.03 to 0.09 mg/kg CR665 in male subjects, maximum serum prolactin concentrations occurred at 30 minutes after the start of the infusion, i.e., 25 minutes after the end of the infusion. Mean $C_{max}$ values were generally similar at the 0.03, 0.06 and 0.09 mg/kg dose levels, with maximum serum prolactin levels being approximately 4- to 6-fold higher than baseline (pre dose) across these dose levels. In female subjects, maximum serum prolactin concentrations occurred at 0.5 to 1 hour after the start of the 5-minute infusion of 0.06 mg/kg CR665. The mean $C_{max}$ value in females was similar to male subjects, with maximum serum prolactin levels being approximately 4-fold greater than baseline (pre dose) in females.

Part A: Pharmacokinetics of CR665 After a One Hour Intravenous Infusion

The plasma concentrations of CR665 following a 1 hour infusion in male subjects are shown in FIGS. 4 and 5.

The pharmacokinetic parameters of CR665 following a 1-hour infusion in male subjects are summarized in Table 8.

TABLE 8

Summary of the Pharmacokinetic Parameters for CR665 Following a 1
hour IV Infusion in Male Subjects (Part A)

| Parameter | 0.015 (N = 4) | 0.03 (N = 4) | 0.06 (N = 4) | 0.12 (N = 4) | 0.24 (N = 4) | 0.36 (N = 4) | 0.42 (N = 4) | 0.48 (N = 8) |
|---|---|---|---|---|---|---|---|---|
| | | | | Dose of (mg/kg) [males] | | | | |
| $AUC_{0-t}$ (ng · h/mL) | 30.0 (20.3) | 70.0 (14.2) | 129 (30.2) | 267 (7.17) | 474 (10.4) | 808 (8.39) | 1080 (17.4) | 1120 (20.5) |

TABLE 8-continued

Summary of the Pharmacokinetic Parameters for CR665 Following a 1 hour IV Infusion in Male Subjects (Part A)

| Parameter | Dose of (mg/kg) [males] | | | | | | | |
|---|---|---|---|---|---|---|---|---|
| | 0.015 (N = 4) | 0.03 (N = 4) | 0.06 (N = 4) | 0.12 (N = 4) | 0.24 (N = 4) | 0.36 (N = 4) | 0.42 (N = 4) | 0.48 (N = 8) |
| $AUC_{0-\infty}$ (ng · h/mL) | 31.4 (21.7) | 72.5 (15.5) | 132 (29.8) | 270 (7.11) | 478 (10.5) | 812 (8.37) | 1084 (17.5) | 1125 (20.4) |
| $C_{max}$ (ng/mL) | 27.8 (15.2) | 65.3 (13.7) | 119 (24.8) | 231 (5.87) | 431 (8.30) | 779 (10.1) | 943 (13.7) | 982 (15.7) |
| $t_{max}^a$ (h) | 1.00 (0.750-1.02) | 1.00 (1.00-1.00) | 0.875 (0.733-1.35) | 0.750 (0.750-1.00) | 1.00 (1.00-1.00) | 1.00 (0.767-1.00) | 1.00 (0.750-1.00) | 0.875 (0.750-1.00) |
| $AUC_{0-t}$ (norm) | 1979 (20.5) | 2349 (14.6) | 2161 (30.1) | 2232 (7.06) | 1979 (10.2) | 2252 (8.40) | 2573 (17.0) | 2333 (20.5) |
| $AUC_{0-\infty}$ (norm) | 2072 (22.0) | 2430 (16.0) | 2201 (29.7) | 2257 (7.00) | 1994 (10.3) | 2263 (8.38) | 2582 (17.1) | 2344 (20.5) |
| $C_{max}$ (norm) | 1837 (15.1) | 2189 (13.8) | 1991 (24.7) | 1932 (5.86) | 1797 (8.12) | 2170 (10.1) | 2248 (13.2) | 2046 (15.9) |
| $t_{1/2}$ (h) | 0.691 (73.2) | 0.732 (50.0) | 0.728 (14.4) | 1.65 (24.0) | 1.37 (17.6) | 1.64 (21.0) | 1.78 (41.8) | 1.87 (36.4) |
| $MRT_{int}$ (h) | 0.512 (43.5) | 0.510 (35.8) | 0.563 (25.7) | 0.723 (23.1) | 0.614 (15.6) | 0.623 (19.8) | 0.618 (17.5) | 0.649 (20.8) |
| CL (mL/min) | 560 (15.2) | 538 (16.0) | 564 (17.8) | 533 (8.71) | 629 (6.47) | 569 (11.5) | 504 (21.3) | 576 (18.6) |
| $V_z$ (L) | 33.5 (60.2) | 34.1 (42.2) | 35.5 (7.44) | 75.9 (20.9) | 74.6 (15.7) | 80.6 (13.3) | 77.9 (22.3) | 93.3 (39.1) |
| $V_{ss}$ (L) | 17.2 (35.4) | 16.5 (31.3) | 19.0 (32.1) | 23.1 (22.3) | 23.2 (18.0) | 21.2 (16.0) | 18.7 (8.42) | 22.4 (20.3) |

Geometric mean (CV %) data are presented
$^a$Median (min-max)
N = Number of subjects studied
(norm) = Normalized for dose and body weight (mg/kg)

During the IV infusion of CR665 at dose levels of 0.015 to 0.48 mg/kg in male subjects, plasma concentrations increased rapidly, with maximum concentrations generally occurring at the end of the 1 hour infusion. Plasma concentrations of CR665 were generally similar at 45 minutes and 1 hour after the start of the infusion for individual subjects at each dose level.

Following the end of the IV infusion, plasma concentrations of CR665 appeared to decline in an essentially biphasic manner with the start of the elimination phase occurring between 1.25 and 6.0 hours after the start of the infusion.

The mean apparent elimination half life was relatively constant in the 0.015 to 0.06 mg/kg dose range, at about 0.7 hours, but became longer across the 0.12 to 0.48 mg/kg dose range, varying from 1.4 to 1.9 hours, with a trend toward longer half life values at higher doses. For individual subjects across the 0.12 to 0.48 mg/kg dose range, the apparent elimination half life ranged from 1.2 to 3.0 hours. This apparent increase in half life at higher dose levels is consistent with plasma concentrations of CR665 being quantifiable for a longer period of time at the higher dose levels, revealing more of the true terminal elimination phase. As a result, statistical analysis showed that the elimination half life for CR665 was dose dependent over the entire dose range.

$AUC_{0-\infty}$ and $C_{max}$ generally appeared to increase in a dose-proportional manner over the dose range of 0.015 to 0.48 mg/kg. This observation was confirmed by statistical analysis, with the estimates of the slopes (95% CI) from the regression analysis for $AUC_{0-\infty}$ and $C_{max}$ being 1.02 (0.978 to 1.06) and 1.02 (0.984 to 1.05). FIG. 6 illustrates the dose-proportional increase in $AUC_{0-\infty}$ for CR665 over the dose range of 0.015 to 0.48 mg/kg.

The dose proportionality of the increase in AUC was found to be almost perfectly linear, as shown in FIG. 6, with an $R^2$ value of 0.98, meaning that, for this data set, 98% of the variation in systemic exposure to CR665 is due to variation in the administered dose of CR665. The importance of this observation is that it enables the practitioner to predict, with a high degree of accuracy, what drug exposures will occur with a given dose of drug. In fact, one skilled in the art can use this information, together with the calculated pharmacokinetic parameters of the drug (see Table 6), to accurately estimate the plasma levels of drug that would result from intravenous infusions of different doses, at what time a steady state concentration of drug would be achieved, and how to design individualized dosage regimens to achieve steady state drug concentrations for a particular patient (Bauer, L. A. *Applied Clinical Pharmacokinetics*, Chap. 2, "Clinical pharmacokinetic equations and calculations", pp. 26 49, 2001). Since controlled release formulations (e.g., microspheres) and devices (e.g., for electrotransport) are intended to provide prolonged steady state drug concentrations, the skilled practitioner utilizes this pharmacokinetic information to define the useful operating characteristics of modes of drug delivery.

Statistical analysis showed that total plasma clearance of CR665 (CL) was dose-independent; however $MRT_{int}$ and the volume of distribution ($V_z$ and $V_{ss}$) were found to be dose-dependent. This was due to the observed change in the elimination rate constant ($\lambda_z$), which was probably due to the fact that the CR665 was quantifiable for a longer period of time, post-injection, at the higher dose levels, rather than true dose-dependency in the kinetics of CR665.

Geometric mean plasma concentrations of CR665 following a 1-hour infusion of 0.24 mg CR665 in female subjects are summarized in FIGS. 7 and 8.

Arithmetic mean plasma concentrations of CR665 following a 1-hour infusion of 0.24 mg/kg CR665 in male and female subjects are summarized in FIG. 9.

The pharmacokinetic parameters of CR665 following a 1-hour infusion of 0.24 mg/kg CR665 in male and female subjects are summarized in Table 9.

TABLE 9

Summary of the Pharmacokinetic Parameters for CR665 Following a 1-hour IV Infusion of 0.24 mg/kg CR665 in Male and Female Subjects (Part A)

| Parameter | 0.24 mg/kg Males (N = 4) | 0.24 mg/kg Females (N = 3) |
|---|---|---|
| $AUC_{0-t}$ (ng·h/mL) | 474 (10.4) | 440 (10.2) |
| $AUC_{0-\infty}$ (ng·h/mL) | 478 (10.5) | 442 (10.1) |
| $C_{max}$ (ng/mL) | 431 (8.30) | 384 (3.03) |
| $t_{max}{}^a$ (h) | 1.00 (1.00-1.00) | 0.750 (0.750-1.00) |
| $AUC_{0-t}$ (norm) | 1979 (10.2) | 1846 (9.71) |
| $AUC_{0-\infty}$ (norm) | 1994 (10.3) | 1855 (9.65) |
| $C_{max}$ (norm) | 1797 (8.12) | 1612 (2.33) |
| $t_{1/2}$ (h) | 1.37 (17.6) | 1.16 (15.9) |
| $MRT_{int}$ (h) | 0.614 (15.6) | 0.515 (12.9) |
| CL (mL/min) | 629 (6.47) | 557 (9.21) |
| $V_z$ (L) | 74.6 (15.7) | 55.7 (12.4) |
| $V_{ss}$ (L) | 23.2 (18.0) | 17.2 (13.1) |

Geometric mean (CV %) data are presented
$^a$Median (min-max)
N = Number of subjects studied
(norm) = Normalized for dose and body weight (mg/kg)

Following administration of 0.24 mg/kg CR665 in female subjects, maximum plasma concentrations were obtained at a similar time to those observed in males, i.e., close to the end of the IV infusion. Thereafter, the disposition kinetics of CR655 were similar in male and female subjects, with a mean terminal elimination half-life of approximately 1.2 to 1.4 hours. At the 0.24 mg/kg dose level, mean values for $AUC_{0-\infty}$, $AUC_{0-\infty}$ (norm), $C_{max}$ and $C_{max}$ (norm) were generally similar in male and female subjects. The between-subject variability for $AUC_{0-\infty}$ and $C_{max}$ was low and similar in male and female subjects at the 0.24 mg/kg dose level. These findings are important because they confirm the predictability of the pharmacokinetics of CR665, which assists the skilled practitioner in the design of alternative dosing regimens that are intended to achieve particular plasma levels of drug over time.

The urinary excretion of CR665 following a 1-hour infusion of 0.24 mg/kg CR665 in male and female subjects is summarized in Table 10.

TABLE 10

Summary of the Urinary Excretion of CR665 Following a 1 hour IV Infusion of 0.24 mg/kg CR665 in Male and Female Subjects (Part A)

| Parameter | 0.24 mg/kg Males (N = 4) | 0.24 mg/kg Females (N = 3) |
|---|---|---|
| $Ae_{0-24\,h}$ (μg) | 631 (39.1) | 446 (30.0) |
| $fe_{0-24\,h}$ (%) | 3.50 (26.2) | 3.02 (23.2) |
| $CL_{R\,0-24\,h}$ (mL/min) | 22.0 (27.9) | 16.8 (22.7) |

Geometric mean (CV %) data are presented
N = Number of subjects studied

The fraction of the dose excreted in the urine as unchanged drug was low in female subjects, and similar to that seen for male subjects.

Part B: Extrapolation of Part A PK Data to Design Brief IV Infusions of CR665

For the Part B studies, five minute infusion dosing protocols were designed using conventional pharmacokinetic calculations (e.g., Bauer, L. A. Applied Clinical Pharmacokinetics, Chap. 2, "Clinical pharmacokinetic equations and calculations", pp. 26 49, 2001), based on the results obtained in the one hour infusion study (Part A). Doses were calculated to produce systemic exposures to CR665 similar to those seen in the one hour infusion study Plasma concentrations of CR665 following a 5-minute infusion in male and female subjects are shown in FIGS. 10 and 11.

The pharmacokinetic parameters of CR665 following a 5-minute infusion in male and female subjects are summarized in Table 11.

TABLE 11

Summary of the Pharmacokinetic Parameters for CR665 Following a 5-minute IV Infusion in Male and Female Subjects (Part B)

| Parameter | Dose of (mg/kg) 0.03 [males] (N = 3) | 0.06 [males] (N = 4) | 0.09 [males] (N = 4) | 0.06 [females] (N = 3) |
|---|---|---|---|---|
| $AUC_{0-t}$ (ng·h/mL) | 65.9 (12.6) | 139 (15.8) | 209 (16.2) | 120 (9.29) |
| $AUC_{0-\infty}$ (ng·h/mL) | 68.4 (11.8) | 142 (16.3) | 213 (16.4) | 122 (8.79) |
| $C_{max}$ (ng/mL) | 233 (14.5) | 624 (32.2) | 783 (19.6) | 520 (18.8) |
| $t_{max}{}^a$ (h) | 0.0833 (0.0833-0.100) | 0.0833 (0.0833-0.0833) | 0.0833 (0.0833-0.0833) | 0.0833 (0.0833-0.0833) |
| $AUC_{0-t}$ (norm) | 2192 (12.3) | 2327 (16.0) | 2318 (16.1) | 2013 (8.92) |

TABLE 11-continued

Summary of the Pharmacokinetic Parameters for CR665 Following a 5-minute IV Infusion in Male and Female Subjects (Part B)

| | Dose of (mg/kg) | | | |
|---|---|---|---|---|
| Parameter | 0.03 [males] (N = 3) | 0.06 [males] (N = 4) | 0.09 [males] (N = 4) | 0.06 [females] (N = 3) |
| $AUC_{0-\infty}$ (norm) | 2273 (11.6) | 2372 (16.5) | 2369 (16.2) | 2044 (8.43) |
| $C_{max}$ (norm) | 7751 (14.4) | 10418 (32.5) | 8701 (19.8) | 8716 (18.4) |
| $t_{1/2}$ (h) | 1.31 (18.3) | 1.00 (13.0) | 1.14 (23.9) | 0.833 (22.4) |
| $MRT_{int}$ (h) | 0.615 (4.48) | 0.502 (26.3) | 0.537 (21.0) | 0.419 (24.2) |
| CL (mL/min) | 473 (7.06) | 553 (15.5) | 575 (14.3) | 544 (9.47) |
| $V_z$ (L) | 53.6 (14.0) | 48.0 (13.4) | 56.7 (33.5) | 39.2 (21.5) |
| $V_{ss}$ (L) | 17.4 (3.13) | 16.6 (24.2) | 18.5 (24.3) | 13.7 (18.8) |

Geometric mean (CV %) data are presented
[a]Median (min-max)
N = Number of subjects studied
(norm) = Normalized for dose and body weight (mg/kg)

Following the IV infusion of CR665 at dose levels of 0.03 to 0.09 mg/kg in male subjects, plasma concentrations increased rapidly with maximum concentrations generally occurring at the end of the 5-minute infusion. Similarly, maximum concentrations of CR665 following administration of 0.06 mg/kg CR665 in female subjects were also attained at the end of the 5 minute infusion. Following the end of the IV infusion, plasma concentrations of CR665 appeared to decline in an essentially biphasic manner, with the start of the elimination phase occurring between 1.0 to 2.0 hours after the start of the infusion in both male and female subjects.

In male subjects, the mean apparent elimination half life, about 1.0 to 1.3 hours, was similar across the 0.03 to 0.09 mg/kg dose range. Statistical analysis confirmed that the elimination half life for CR665 was independent of dose. The disposition kinetics of CR655 were similar in male and female subjects, with the mean terminal elimination half life of CR665 being approximately 0.8 hours in females at the 0.06 mg/kg dose level.

In male subjects, $AUC_{0-\infty}$ and $C_{max}$ generally appeared to increase in a dose-proportional manner over the dose range 0.03 to 0.09 mg/kg. This was confirmed by statistical analysis, with the estimates of the slopes (95% CI) from the regression analysis for $AUC_{0-\infty}$ and $C_{max}$ being 1.04 (0.853 to 1.22) and 1.12 (0.800 to 1.44). FIG. 12 illustrates the dose-proportional increase in $AUC_{0-\infty}$ for CR665 over the dose range of 0.03 to 0.09 mg/kg in male subjects.

At the 0.06 mg/kg dose level, mean values for $AUC_{0-\infty}$, $AUC_{0-\infty}$ (norm), $C_{max}$ and $C_{max}$ (norm) were generally similar in male and female subjects following a 5-minute infusion.

Mean values for $MRT_{int}$, CL, $V_z$ and $V_{ss}$ were similar across the 0.03 to 0.09 mg/kg dose range in male subjects, which was confirmed by statistical analysis. Mean values for each parameter were also similar for male and female subjects at the 0.06 mg/kg dose level.

In general, low between-subject variability was noted for $AUC_{0-\infty}$ and $C_{max}$ in male subjects, with CV % values ranging from 11.8 to 16.4% and 19.6% to 32.2%, respectively. Across all doses in male subjects, the pooled between-subject variability for $AUC_{0-\infty}$ and $C_{max}$ was 15.3% and 24.1%, respectively. The between-subject variability for $AUC_{0-\infty}$ and $C_{max}$ was also low in female subjects at the 0.24 mg/kg dose level, with CV % values of 8.8% and 18.8%, respectively.

The urinary excretion of CR665 following a 5-minute infusion in male and female subjects is summarized in Table 12:

TABLE 12

Summary of the Urinary Excretion of CR665 Following a 5-minute IV Infusion in Male and Female Subjects (Part B)

| | Dose of (mg/kg) | | | |
|---|---|---|---|---|
| Parameter | 0.03 [males] (N = 3) | 0.06 [males] (N = 4) | 0.09 [males] (N = 4) | 0.06 [females] (N = 3) |
| $Ae_{0-24h}$ (µg) | 70.0 (27.3) | 157 (25.8) | 262 (13.5) | 153 (16.9) |
| $fe_{0-24h}$ (%) | 3.60 (29.6) | 3.33 (27.6) | 3.56 (7.29) | 3.83 (24.0) |
| $CL_{R\,0-24h}$ (mL/min) | 17.1 (22.7) | 18.4 (24.6) | 20.5 (12.0) | 20.9 (17.7) |

Geometric mean (CV %) data are presented
N = Number of subjects studied

In male subjects, the fraction of the dose excreted in the urine as unchanged drug was low for all dose levels, with approximately 3.5% being eliminated up to 24 hours post-dose. The fraction of unchanged drug excreted in the urine was also low in female subjects (3.8%), and similar to male subjects.

The amount of CR665 excreted in the urine increased in a dose proportional manner over the dose range studied in male subjects. This was confirmed by statistical analysis, with the slopes of the regression not being significantly different from unity. Renal clearance was generally low and similar across all dose levels, with dose independence being confirmed by statistical analysis.

The results of the statistical analyses to assess the effect of infusion time on the pharmacokinetic parameters of CR665 in male subjects are presented in Table 13.

TABLE 13

Statistical Analysis of the Effect of Infusion Time on the Pharmacokinetic Parameters for CR665 in Male Subjects (Parts A & B)

| Parameter | Geometric least squares means | | Ratio of geometric least squares means 5-minute:1-hour | 90% CI for the ratio | 95% CI for the ratio |
|---|---|---|---|---|---|
| | 5-minute infusion | 1-hour infusion | | | |
| $AUC_{0-t}$ (norm) | 2286 | 2238 | 1.02 | 0.957 to 1.09 | 0.944 to 1.11 |
| $AUC_{0-\infty}$ (norm) | 2343 | 2260 | 1.04 | 0.971 to 1.11 | 0.957 to 1.12 |
| $C_{max}$ (norm) | 9002 | 2003 | 4.49 | 3.98 to 5.08 | 3.87 to 5.22 |
| $t_{1/2}$ (h) | 1.28 | 1.25 | 1.02 | 0.804 to 1.29 | 0.762 to 1.37 |
| $MRT_{int}$ (h) | 0.558 | 0.605 | 0.923 | 0.817 to 1.04 | 0.794 to 1.07 |
| CL (mL/min) | 538 | 557 | 0.964 | 0.903 to 1.03 | 0.889 to 1.05 |
| $V_z$ (L) | 61.0 | 59.1 | 1.03 | 0.825 to 1.29 | 0.784 to 1.36 |
| $V_{ss}$ (L) | 18.1 | 20.1 | 0.900 | 0.804 to 1.01 | 0.783 to 1.03 |
| $fe_{0-24\,h}$ (%) | 3.48 | 3.46 | 1.01 | 0.908 to 1.12 | 0.887 to 1.15 |

(norm) = Normalized for dose and body weight (mg/kg)

In male subjects, the following pharmacokinetic parameters for CR665 were similar following an IV infusion time of 1-hour versus 5-minutes: $AUC_{0-\infty}$, $AUC_{0-t}$, $t_{1/2}$, CL, $V_z$, $V_{ss}$, and $fe_{0-24\,h}$, suggesting that the overall systemic exposure to CR665, based upon AUC and disposition kinetics, were not affected by the different infusion times. The only parameter, however, for which the statistical analysis confirmed a significant difference was $C_{max}$, which was, as expected, approximately 4.5-fold higher for the 5-minute compared to the 1-hour infusion.

The statistical analyses of the effect of infusion time on the pharmacokinetic parameters of CR665 in female subjects are presented in Table 14.

TABLE 14

Statistical Analysis of the Effect of Infusion Time on the Pharmacokinetic Parameters for CR665 in Female Subjects

| Parameter | Geometric least squares means | | Ratio of geometric least squares means 5-minute:1-hour | 90% CI for the ratio | 95% CI for the ratio |
|---|---|---|---|---|---|
| | 5-minute infusion | 1-hour infusion | | | |
| $AUC_{0-t}$ (norm) | 2013 | 1936 | 1.04 | 0.918 to 1.18 | 0.893 to 1.21 |
| $AUC_{0-\infty}$ (norm) | 2044 | 1943 | 1.05 | 0.928 to 1.19 | 0.903 to 1.23 |
| $C_{max}$ (norm) | 8716 | 1655 | 5.27 | 4.17 to 6.66 | 3.96 to 7.01 |
| $t_{1/2}$ (h) | 0.946 | 1.05 | 0.901 | 0.606 to 1.34 | 0.554 to 1.47 |
| $MRT_{int}$ (h) | 0.430 | 0.498 | 0.864 | 0.708 to 1.06 | 0.677 to 1.10 |
| CL (mL/min) | 544 | 573 | 0.950 | 0.837 to 1.08 | 0.813 to 1.11 |
| $V_z$ (L) | 45.7 | 50.2 | 0.911 | 0.628 to 1.32 | 0.577 to 1.44 |
| $V_{ss}$ (L) | 14.1 | 17.0 | 0.832 | 0.692 to 1.00 | 0.664 to 1.04 |
| $fe_{0-24\,h}$ (%) | 3.83 | 2.70 | 1.42 | 1.16 to 1.73 | 1.11 to 1.81 |

(norm) = Normalized for dose and body weight (mg/kg)

In female subjects, the following pharmacokinetic parameters for CR665 were similar following an IV infusion time of 1-hour versus 5-minutes: $AUC_{0-\infty}$, $AUC_{0-\infty}$, $t_{1/2}$, CL, $V_z$, $V_{ss}$ and $fe_{0-24\ h}$ suggesting that the overall systemic exposure to CR665, based upon AUC and disposition kinetics, were not affected by the different infusion times. However, as would be expected, $C_{max}$ was significantly higher (5.3-fold) for the 5-minute compared to the 1-hour infusion. These findings reinforce the predictability of the pharmacokinetics of CR665, which aids the skilled practitioner in the design of drug administration protocols that are designed to achieve a particular level of systemic exposure to drug without undue experimentation.

Pharmacodynamic—Pharmacokinetic Relationship

The relationship between pharmacodynamic parameters of serum prolactin (changes from baseline) and pharmacokinetic parameters of CR665 following IV infusions of 0.015 to 0.36 mg/kg in male subjects is presented in FIGS. 13 and 14.

In Part A, there was a direct linear correlation between serum concentrations of prolactin (based on $AUC_{0-12}$ h and $C_{max}$) and the plasma concentration of CR665 (based on $AUC_{0-\infty}$ and $C_{max}$) over the 0.015 to 0.36 mg/kg dose range following a 1-hour infusion in male subjects, with correlation coefficients of 0.667 and 0.565 for AUC and $C_{max}$ values, respectively. The $AUC_{0-12\ h}$ and $C_{max}$ values for serum prolactin appeared to plateau at higher $AUC_{0-\infty}$ and $C_{max}$ values for CR665 associated with dose levels of 0.36 to 0.48 mg/kg, indicating that the maximum increase in serum prolactin had been achieved by 0.36 mg/kg CR665 administered as a 1-hour infusion.

In Part B, there was no apparent correlation between serum prolactin concentrations and plasma CR665 concentrations in male subjects following a 5-minute infusion. A likely cause of the absence of a correlation is the temporal dissociation of pharmacokinetics and pharmacodynamics in these subjects: while plasma CR665 concentrations peaked at the end of the 5-minute infusion and declined thereafter, serum prolactin concentrations only began to significantly rise at 10 minutes (5 minutes after the end of the infusion), and continued to rise at 30 minutes, with substantial but declining levels measured at 60 minutes. Under these conditions, a correlation between plasma CR665 concentrations and serum prolactin concentrations would not be expected. However, with longer (e.g., 1 hour) infusions of CR665, the plasma concentration of CR665 may better reflect the concentration of CR665 in the pharmacodynamically relevant compartment (i.e., high affinity kappa opioid receptors), and thereby yield the significant linear relationship shown in FIGS. 13 and 14.

Following administration of 0.015 to 0.48 mg/kg CR665 as a 1-hour infusion in male subjects, $AUC_{0-\infty}$ and $C_{max}$ increased in a dose-proportional manner over the entire dose range. The between-subject variability in the pharmacokinetics of CR665 was low in male subjects.

In female subjects, maximum plasma concentrations of CR665 occurred at the end of the 1-hour infusion period following a 0.24 mg/kg dose, which was similar to male subjects. The systemic exposure of CR665, based on $AUC_{0-\infty}$ and $C_{max}$, was similar in male and female subjects. The disposition of CR665 was also similar between genders, with a mean terminal elimination half-life of 1.2 hours in female subjects. Furthermore, similar between-subject variability was observed in male and female subjects.

The duration of infusion had no effect on the overall systemic exposure to CR665, with $AUC_{0-\infty}$ being similar following the 1-hour and 5-minute infusions in both male and female subjects. However, maximum plasma concentrations of CR665 were notably higher following the 5-minute infusion compared to the 1-hour infusion, being approximately 4.5-fold higher in male subjects and 5.3-fold higher in female subjects. The difference in $C_{max}$ was expected because of the higher rate of infusion used for the 5-minute infusion (360 mL/hour) compared to the 1-hour infusion (30 mL/hour). The disposition kinetics of CR665 was similar for the 1-hour and 5-minute infusion, and low between-subject variability was observed for both infusion times.

The apparent volume of distribution at steady state ($V_{SS}$) of CR665 in male subjects ranged from 19 to 23 L over the 0.12 to 0.48 mg/kg dose range, which is similar to the volume of extracellular fluid, and is consistent for a peptide with limited ability to penetrate lipid containing membranes. This observation reflects another aspect of the present invention: a relatively low volume of distribution. The volume of distribution is a quantitative measure of the extent of distribution of drug outside the vasculature; it is the apparent volume which would contain the entire amount of drug in the body at the same concentration it is present in the blood. In general, a compound with a low volume of distribution will have physical characteristics that impede transport across biological membranes. Thus, a polar compound with a low apparent volume of distribution, such as CR665, would not be expected to cross the blood-brain barrier as well as lipid-soluble compounds that typically have a higher apparent volume of distribution, and a greater propensity to cross the blood-brain barrier.

All patents and other references cited herein are hereby incorporated by reference.

Other embodiments are within the following claims.

What is claimed is:

1. A method of elevating or stabilizing levels of serum prolactin in a mammal in need of elevated or stabilized levels of serum prolactin, comprising administering to said mammal an amount of a peripherally selective kappa opioid receptor agonist, a salt thereof or a pro-drug thereof effective to elevate or stabilize levels of serum prolactin in the mammal.

2. The method of claim 1, wherein said peripherally selective kappa opioid receptor agonist, a salt thereof or a pro-drug thereof comprises a peptide.

3. The method of claim 2, wherein said peptide has a binding affinity for the kappa opioid receptor that is 1,000 or more times greater than its binding affinity for non-kappa opioid receptors.

4. The method of claim 2, wherein said peptide has the formula:

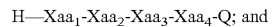

H—Xaa$_1$-Xaa$_2$-Xaa$_3$-Xaa$_4$-Q; and wherein Xaa$_1$ is (A)D-Phe, (C$^{alpha}$ Me)D-Phe, D-Tyr, D-Tic or D-Ala(cyclopentyl or thienyl), with A being H, NO$_2$, F, Cl or CH$_3$; Xaa$_2$ is (A')D-Phe, D-1Nal, D-2Nal, D-Tyr or D-Trp, with A' being A or 3,4Cl$_2$; Xaa$_3$ is D-Nle, (B)D-Leu, D-Hle, D-Met, D-Val, D-Phe or D-Ala(cyclopentyl) with B being H or C$^{alpha}$ Me; Xaa$_4$ is D-Arg, D-Har, D-nArg, D-Lys, D-Lys (Ipr), D-Arg(Et$_2$), D-Har(Et$_2$), D-Amf(G), D-Dbu, (B)D-Orn or D-Orn(Ipr), with G being H or amidino; and Q is NR$_1$R$_2$, morpholinyl, thiomorpholinyl, (C)piperidinyl, piperazinyl, 4-mono- or 4,4-di-substituted piperazinyl or delta-ornithinyl, with R$_1$ being lower alkyl, substituted lower alkyl, benzyl, substituted benzyl, aminocyclohexyl, 2-thiazolyl, 2-picolyl, 3-picolyl or 4-picolyl, R$_2$ being H or lower alkyl; and C being H, 4-hydroxy or 4-oxo.

5. The method of claim 4, wherein Q is morpholinyl or thiomorpholinyl.

6. The method of claim 4, wherein Q is NHR$_1$, and R$_1$ is 4-picolyl.

7. The method of claim 2, wherein said peptide has the formula:

H—Xaa$_1$-Xaa$_2$-Xaa$_3$-Xaa$_4$-Q; and wherein Xaa$_1$ is D-Phe (unsubstituted or substituted by C$^{alpha}$Me, 2F, 4F or 4Cl) or D-Ala(cyclopentyl or thienyl); Xaa$_2$ is (A')D-Phe, D-1Nal, D-2Nal or D-Trp, with A' being H, 4F, 4Cl, 4NO$_2$ or 3,4Cl$_2$; Xaa$_3$ is D-Nle, D-Leu, D-CML, D-Met or D-Acp; Xaa$_4$ is D-Arg, D-Arg(Et$_2$), D-Lys, D-Ily, D-Har, D-Har(Et$_2$), D-nArg, D-Orn, D-Ior, D-Dbu, D-Amf, and D-Amf(Amd); and Q is NR$_1$R$_2$, Mor, Tmo, Pip, 4-Hyp, OxP or Ppz, with R$_1$ being Me, Et, Pr, Bu, hEt, Cyp, Bzl or 4-picolyl, and R$_2$ being H or Et.

8. The method of claim 7, wherein Xaa$_2$ is D-Phe, Xaa$_3$ is D-Nle and Xaa$_4$ is D-Arg.

9. The method of claim 7, wherein Q is morpholinyl or thiomorpholinyl.

10. The method of claim 7, wherein Q is NHR$_1$, and R$_1$ is 4-picolyl.

11. The method of claim 7, wherein Xaa$_3$ is D-Nle or D-Leu and Q is morpholinyl.

12. The method of claim 7, wherein Xaa$_1$ is D-Phe, D-4Fpa, D-2Fpa, D-Acp or D-Ala(2Thi); Xaa$_2$ is (A)D-Phe, D-1Nal, D-2Nal or D-Trp, with A being 4F or 4Cl; Xaa$_3$ is D-Nle, D-Met or D-Leu; Xaa$_4$ is D-Arg, D-Har, D-nArg, D-Lys, D-Orn or D-Amf(Amd); and Q is NHR$_1$, Mor, Tmo, Pip or Ppz, with R$_1$ being Et, Pr or 4Pic.

13. The method of claim 2, wherein said peptide has the formula: H-D-Phe-D-Phe-D-Nle-D-Arg-NHEt, H-D-Phe-D-Phe-D-Nle-D-Arg-morpholinyl, H-D-Phe-D-Phe-D-Nle-D-Arg-NH-4-picolyl, H-D-Phe-D-Phe-D-Nle-D-Arg-NHPr, H-D-Phe-D-Phe-D-Nle-D-Arg-thiomorpholinyl, H-D-Phe-D-Phe-D-Nle-D-Arg-NEt$_2$, H-D-Phe-D-Phe-D-Nle-D-Arg-NHMe, H-D-Phe-D-Phe-D-Leu-D-Orn-morpholinyl, H-D-Phe-D-Phe-D-Phe-D-Nle-D-Arg-NHhEt, H-D-Phe-D-Phe-D-Nle-D-Arg-NH-cyclopropyl, H-D-Ala(2Thi)-D-4Cpa-D-Leu-D-Arg-morpholinyl, H-D-Phe-D-Phe-D-Nle-D-Arg-piperidinyl, H-D-Phe-D-Phe-D-Leu-D-Orn-NHEt, H-D-Phe-D-Phe-D-Leu-D-Lys-morpholinyl, or H-D-Phe-D-Phe-D-Nle-D-Arg-piperazinyl.

14. The method of claim 1, wherein said peripherally selective kappa opioid receptor agonist, when administered peripherally, does not substantially cross the blood-brain barrier.

15. The method of claim 1, wherein said administration comprises intravenous, subcutaneous, intramuscular, intranasal, oral, or transdermal administration.

16. The method of claim 15, wherein said transdermal administration is provided by an electrotransport device.

17. The method of claim 16, wherein said administration is through a body surface and comprises:
    (a) providing a first electrode;
    (b) providing a second electrode;
    (c) providing a power source electrically connected to said first and said second electrodes;
    (d) providing at least one donor reservoir having the peripherally selective kappa opioid receptor agonist, wherein said donor reservoir is associated with said first or second electrode; and
    (e) delivering a therapeutically effective amount of said peripherally selective kappa opioid receptor agonist through said body surface.

18. A method of treating a mammal in need of elevated or stabilized prolactin levels, said method comprising administering to said mammal an amount of a peripherally selective kappa opioid receptor agonist or a salt thereof or a pro-drug thereof, and administering, either separately or in combination with said peripherally selective kappa opioid receptor agonist or a salt thereof or a pro-drug thereof, an amount of an additional prolactin elevating compound, effective to treat the mammal.

19. The method of claim 18, wherein the prolactin-elevating compound is a D2 dopamine receptor antagonist or a mu opioid receptor agonist.

20. A method for treating insufficient or inadequate lactation, or for preventing insufficient or inadequate lactation, in a mammal, comprising administering an amount of a peripherally selective kappa opioid receptor agonist or a salt thereof or a pro-drug thereof, effective to treat or prevent insufficient or inadequate lactation in the mammal.

21. The method of claim 20, wherein such amount of a peripherally selective kappa opioid receptor agonist or a salt thereof or a pro-drug thereof is administered to said mammal prior to or after childbirth in conjunction with a lactation enhancer or stabilizer effective to treat said mammal.

22. The method of claim 21, wherein the lactation enhancer comprises oxytocin.

* * * * *